(12) United States Patent
Fainstain

(10) Patent No.: US 11,899,844 B2
(45) Date of Patent: *Feb. 13, 2024

(54) ROBUST MOTION SICKNESS REDUCTION DEVICE

(71) Applicant: NeuroHaptics, Inc., Austin, TX (US)

(72) Inventor: Evgene Fainstain, San Jose, CA (US)

(73) Assignee: NEUROHAPTICS, INC., Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/112,407

(22) Filed: Feb. 21, 2023

(65) Prior Publication Data

US 2023/0280830 A1 Sep. 7, 2023

Related U.S. Application Data

(63) Continuation of application No. 17/750,246, filed on May 20, 2022, now Pat. No. 11,586,291, and a continuation of application No. 17/750,243, filed on May 20, 2022, now Pat. No. 11,599,198, which is a continuation of application No. 17/695,699, filed on Mar. 15, 2022, now abandoned, said application No. (Continued)

(51) Int. Cl.
*G06F 3/01* (2006.01)
*G06F 1/16* (2006.01)

(52) U.S. Cl.
CPC ............ *G06F 3/016* (2013.01); *G06F 1/163* (2013.01); *G06F 3/015* (2013.01)

(58) Field of Classification Search
CPC .......... G06F 3/016; G06F 1/163; G06F 3/015; A61M 2021/0022; A61M 2021/0027; A61M 2021/0066; A61M 2021/0072; A61M 2205/3306; A61M 2205/332; A61M 2205/3368; A61M 2205/3375; A61M 2205/3553; A61M 2205/3561; A61M 2205/3569; A61M 2205/3592; A61M 2205/505; A61M 2205/8206; A61M 2205/84; A61M 2209/088; A61M 2230/63; A61M 21/00; A61B 5/1114; A61B 5/4023; A61B 5/486; A61B 5/6814; A61B 5/7455
See application file for complete search history.

(56) References Cited

U.S. PATENT DOCUMENTS 6,443,913 B1 9/2002 Kania
6,932,090 B1 * 8/2005 Reschke ............... G02C 5/001
128/897
(Continued)

*Primary Examiner* — William Lu
(74) *Attorney, Agent, or Firm* — Galvin Patent Law LLC; Brian R. Galvin

(57) ABSTRACT

A device for motion sickness reduction. The device operates by providing haptic feedback using transducers that convert electrical signals to a tactile sensation such as pressure, vibration, electrical stimulation, temperature, or airflow. The transducers are located at different locations on the body of a user, and actively change their operation to indicate a direction of motion or rotation to the user through haptic (tactile) feedback. This tactile feedback can be used to reduce motion sickness. In an embodiment, the feedback is improved by deducting motion associated with the user's visual frame of reference from motion associated with the user's vestibular frame of reference.

18 Claims, 26 Drawing Sheets

Related U.S. Application Data

17/750,246 is a continuation-in-part of application No. 17/695,699, filed on Mar. 15, 2022, now abandoned, which is a continuation of application No. 15/930,119, filed on May 12, 2020, now Pat. No. 11,275,441.

(60) Provisional application No. 62/846,674, filed on May 12, 2019.

(56) References Cited

U.S. PATENT DOCUMENTS

| | | | | |
|---|---|---|---|---|
| 7,843,158 | B2 * | 11/2010 | Prisco | A61B 34/30 318/566 |
| 8,620,473 | B2 * | 12/2013 | Diolaiti | A61B 34/72 600/407 |
| 9,149,222 | B1 * | 10/2015 | Zets | A61B 5/4023 |
| 9,333,042 | B2 | 5/2016 | Diolaiti et al. | |
| 9,704,230 | B2 | 7/2017 | Hofmann et al. | |
| 9,754,167 | B1 * | 9/2017 | Holz | G06F 3/011 |
| 9,999,835 | B2 * | 6/2018 | Watson | G16H 50/20 |
| 10,258,259 | B1 * | 4/2019 | Zets | A61B 5/7455 |
| 10,657,655 | B2 * | 5/2020 | Ro | G06V 40/20 |
| 10,765,856 | B2 | 9/2020 | Wong et al. | |
| 10,926,773 | B2 * | 2/2021 | Vulcu | B60N 2/34 |
| 11,275,441 | B2 * | 3/2022 | Fainstain | A61M 21/00 |
| 2003/0088294 | A1 * | 5/2003 | Gesotti | A61N 1/36003 607/45 |
| 2014/0176296 | A1 * | 6/2014 | Morgan | G06F 3/011 340/4.13 |
| 2014/0222021 | A1 * | 8/2014 | Diolaiti | A61B 90/361 606/130 |
| 2015/0049589 | A1 * | 2/2015 | Dooley | G10K 11/17825 367/137 |
| 2015/0068052 | A1 * | 3/2015 | Krueger | G01C 9/16 33/301 |
| 2015/0273179 | A1 * | 10/2015 | Krueger | G02C 11/00 600/27 |
| 2015/0301797 | A1 * | 10/2015 | Miller | G06F 3/011 345/156 |
| 2016/0089298 | A1 * | 3/2016 | Owen | A61H 23/0245 601/47 |
| 2016/0136104 | A1 * | 5/2016 | Niichel | A61K 41/0028 424/452 |
| 2017/0143935 | A1 * | 5/2017 | Hanbury | A61M 21/02 |
| 2018/0004286 | A1 * | 1/2018 | Chen | G06F 3/012 |
| 2018/0133102 | A1 * | 5/2018 | Owen | A61F 11/14 |
| 2018/0157317 | A1 * | 6/2018 | Richter | G06T 19/006 |
| 2018/0256444 | A1 * | 9/2018 | Owen | A61H 23/0245 |
| 2018/0264266 | A1 * | 9/2018 | Owen | A61F 11/04 |
| 2019/0041989 | A1 * | 2/2019 | Wu | G06T 7/90 |
| 2019/0167095 | A1 * | 6/2019 | Krueger | A61B 3/113 |
| 2020/0001085 | A1 | 1/2020 | Owen et al. | |
| 2022/0008746 | A1 * | 1/2022 | Malchano | A61B 5/0036 |

* cited by examiner

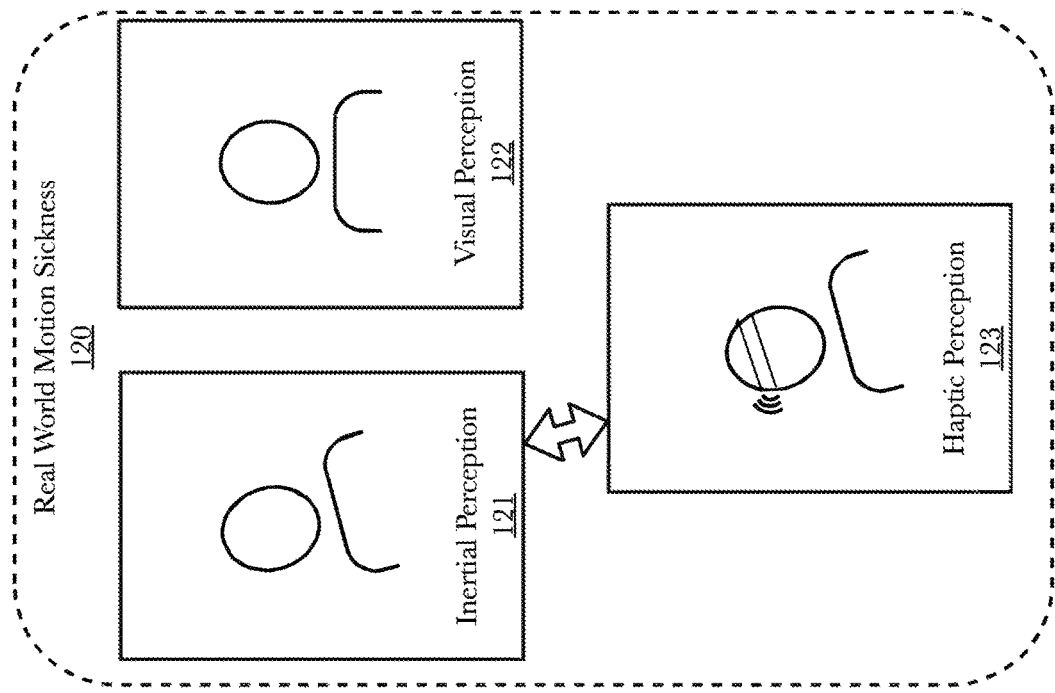
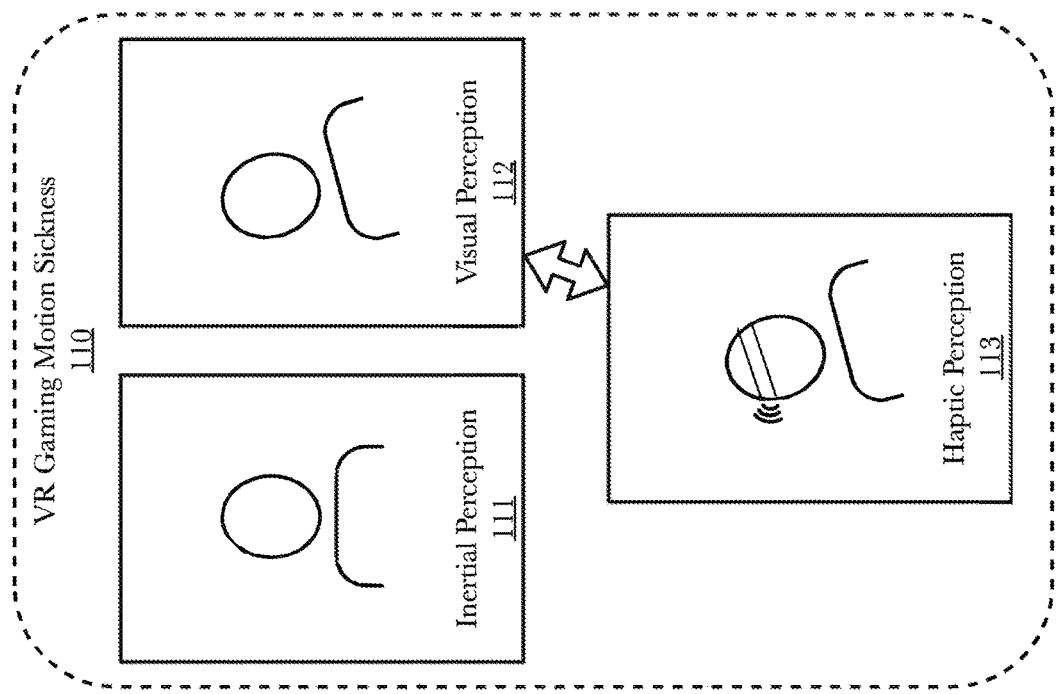
Fig. 1

701 Obtain an input comprising a direction of motion and a magnitude of motion from a sensor or other device 702 Operate one or more transducers in the direction of motion relative to the user indicated by the input 703 Adjust the intensity of the operated transducers according to the magnitude of the input and/or the direction of the transducer versus the direction of motion

ROBUST MOTION SICKNESS REDUCTION DEVICE

CROSS-REFERENCE TO RELATED APPLICATIONS

Priority is claimed in the application data sheet to the following patents or patent applications, each of which is expressly incorporated herein by reference in its entirety:
Ser. No. 17/750,246
Ser. No. 17/750,243
Ser. No. 17/695,699
Ser. No. 15/930,119
62/846,674

BACKGROUND OF THE INVENTION

Field of the Art

The disclosure relates to the field of haptic feedback and stimulation, and more particularly to the fields of motion sickness reduction, directional indication using haptic feedback, and neural rehabilitation using haptic stimulation.

Discussion of the State of the Art

Motion sickness is a common problem, but existing methods for reducing motion sickness are not ideal. Motion sickness occurs when a person's inertial perception of motion from the inner ear conflicts with the person's visual perception of motion. This commonly occurs during vehicular travel such as riding in a car, train, boat, or airplane, and is particularly troublesome when the person cannot view the motion of the vehicle (for example, while reading in a moving car, or while riding in the interior of a boat). Motion sickness has become a significant problem when playing virtual reality games, wherein the user's inner ear perceives a different motion than the user's eyes perceive.

Some existing methods for reducing motion sickness include acupuncture, acupressure (including wristbands that put pressure on certain parts of the wrist), aromatherapy, and herbal teas, which are all of dubious effect. Medications do work, but generally have side effects such as sleepiness. There exists a need for a wearable device that enhances human sensory inputs by providing feedback regarding the direction and distance of objects, especially for people suffering from vision impairment.

Further, for stroke patients suffering from a varying degree of brain damage, the conventional treatment approach consists of mainly "isolated" neural rehabilitation routines, such as specific bodily movements, speech therapy, and stationary video gameplays. There exists a need for a connected, more effective approach that combines existing or new neural rehabilitation routines with haptic stimulation of targeted brain regions.

What is needed is a device for reducing motion sickness that is effective but does not have the side effects of medications, allows for provision of directional feedback to the user, and further provides an improved approach to existing neural rehabilitation routines.

SUMMARY OF THE INVENTION

Accordingly, the inventor has conceived and reduced to practice, a device for motion sickness reduction. The device operates by providing haptic feedback using transducers that convert electrical signals to a tactile sensation such as pressure, vibration, electrical stimulation, temperature, or airflow. The transducers are located at different locations on the body of a user, and actively change their operation to indicate a direction of motion or rotation to the user through haptic (tactile) feedback. This tactile feedback can be used to reduce motion sickness. In an embodiment, the feedback is improved by deducting motion associated with the user's visual frame of reference from motion associated with the user's vestibular frame of reference.

According to a first preferred embodiment, a device for motion sickness reduction associated with physical movement is disclosed, comprising: an annular-shaped headband configured to be worn about a horizontal circumference of a human head, the headband having a circumference and comprising: a plurality of transducers arranged about the circumference of the headband, each transducer being configured to provide haptic feedback to a wearer of the headband; and a first sensor configured to periodically measure motion of the headband; a second sensor configured to periodically measure motion of an external reference frame within which the wearer is located; a controller comprising a processor, a memory, and a plurality of programming instructions stored in the memory which, when operating on the processor, cause the controller to: periodically receive motion data from the first and second sensor, the motion data indicating the direction and the magnitude of the motion of the headband and the external reference frame; determine the difference between the motion of the external reference frame and the motion of the headband; identify a first transducer of the plurality of transducers that is closest in direction to the direction of the difference in motion; operate the first transducer, the intensity of transducer operation corresponding to the magnitude of the motion; while the magnitude of the motion meets or exceeds a threshold value, operate a second transducer to the left of the first transducer and a third transducer to the right of the first transducer, the intensity of operation of the second and third transducers corresponding to the magnitude of the motion, but at a lower intensity than the operation of the first transducer; while the magnitude of the difference in motion falls below the threshold value, cease the operation of the second and third transducers; and repeat the operations of the controller set forth above periodically as the difference in motion data is periodically computed as data is received from the sensor.

According to a second preferred embodiment, a method for motion sickness reduction associated with physical movement is disclosed, comprising the steps of: periodically receiving motion data from a first and a second sensor, the motion data indicating the direction and the magnitude of the motion of a headband and an external reference frame; determining the difference between the motion of the vehicle and the motion of the headband; identifying a first transducer of the plurality of transducers that is closest in direction to the direction of the difference in motion; operating the first transducer, the intensity of transducer operation corresponding to the magnitude of the motion; while the magnitude of the motion meets or exceeds a threshold value, operating a second transducer to the left of the first transducer and a third transducer to the right of the first transducer, the intensity of operation of the second and third transducers corresponding to the magnitude of the motion, but at a lower intensity than the operation of the first transducer; while the magnitude of the difference in motion falls below the threshold value, ceasing the operation of the second and third transducers; and repeating the operations of the controller set forth above periodically as the difference in motion data is periodically computed as data is received from the sensor.

According to various aspects; wherein the motion data comprises one or a combination of the headband's position, speed, velocity, or acceleration; wherein, when a new direction of the motion is contained in a periodic receipt of motion data from the sensor or the input port and a newly-selected first transducer is selected by the controller to reflect the new direction, one or more transducers are activated in sequence between the previously-selected first transducer and the newly-selected first transducer to indicate a rotational transition from the old direction to the new direction; wherein the intensity of operation of the one or more transducers activated in sequence is gradually reduced in the reverse order of their activation so as to cause a trailing off of intensity following the indication of rotational transition; wherein the haptic feedback is in the form of pressure, vibration, or electrical stimulation; wherein the sensor can be located at any position on the headband.

BRIEF DESCRIPTION OF THE DRAWINGS

The accompanying drawings illustrate several aspects and, together with the description, serve to explain the principles of the invention according to the aspects. It will be appreciated by one skilled in the art that the particular arrangements illustrated in the drawings are merely exemplary and are not to be considered as limiting of the scope of the invention or the claims herein in any way.

FIG. 1 is a diagram illustrating the causes of motion sickness, and illustrating how a third motion perception input may reduce motion sickness.

FIG. 7 is a diagram illustrating an exemplary method for motion sickness reduction.

DETAILED DESCRIPTION OF THE DRAWINGS

Figure 2:
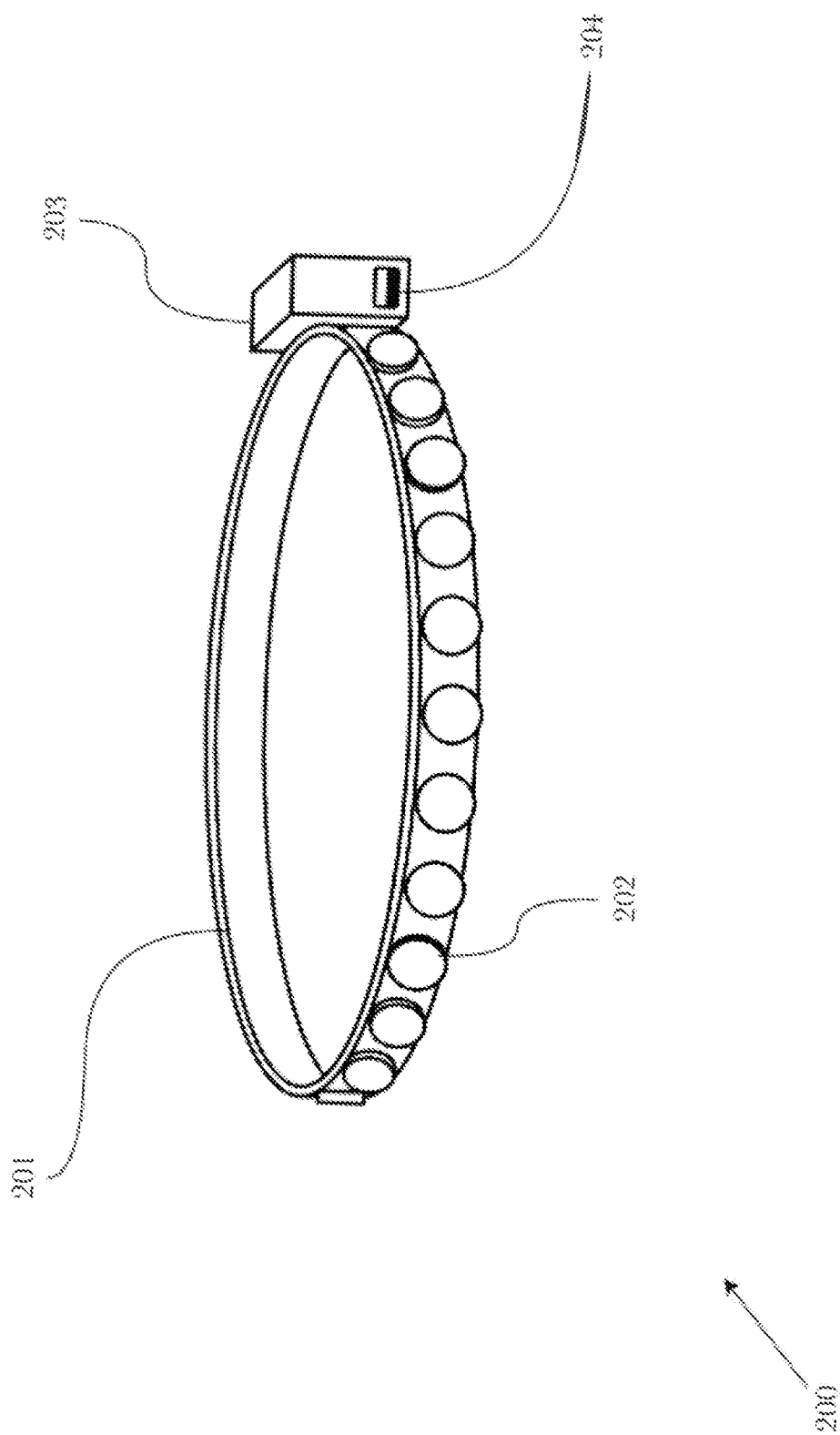
FIG. 2 is a diagram illustrating an exemplary embodiment of a device for motion sickness reduction and directional indication.

The inventor has conceived, and reduced to practice, a device for reducing motion sickness reduction, directional indication, and neural rehabilitation. The device provides haptic feedback using transducers that convert electrical signals to a tactile sensation such as pressure, vibration, electrical stimulation, temperature, or airflow. The transducers are located at different locations on the body of a user, and actively change their operation to indicate a direction of motion or rotation to the user through haptic (tactile) feedback. In motion sickness mode, the device provides a third motion perception input using the body's somatosensory system to overcome the conflict in inertial perception of motion and visual perception of motion. This tactile feedback provides the user with a third motion perception input that acts as a "tie-breaker" in the conflict in the user's inertial perception of motion and visual perception of motion, reducing the perceived conflict and thereby reducing the user's motion sickness. In directional input mode, the device senses or receives the relative locations of the user and a target location, and provides haptic feedback to the user in the direction of the target location, adjusting the strength of the feedback to indicate the distance from the user to the target location. In neural rehabilitation mode, the device receives input regarding a rehabilitation task to be performed, and provides haptic feedback to the user's head at the location corresponding to the part of the brain that is associated with the rehabilitation task.

Motion sickness is caused by a conflict between perceptions of motion by the inertial sensor of the inner ear and the visual sensor of the eyes. The fluid inside the inner ear acts as an inertial sensor, shifting inside the ear whenever the body is in motion, whether such motion is linear or rotational. The inner ear detects the shift in fluid and sends signals associated with that shift to the brain, which interprets the signals as motion. The eyes act as a visual sensor of motion, detecting changes in the location of objects in the field of view when the body is in motion. The eyes likewise send signals to the brain, which interprets those signals as motion. Normally, the signals received by the brain from the eyes and inner ears correspond. When one is walking forward, for example, the inner ear perceives the forward motion through inertial changes, and the eyes perceive the forward motion through visual changes. The brain receives these corresponding signals, the signals match the brain's expectations for movement, and the brain indicates that all is fine.

However, when the signals received by the brain from the eyes and inner ears do not match, the brain perceives a conflict, which it cannot resolve, and indicates that something is wrong by causing nausea, or motion sickness. Because there are two primary sensors for motion, there are two primary ways in which motion sickness can occur. First, motion sickness can occur when the inner ear correctly perceives motion, but the eyes incorrectly do not. Second, motion sickness can occur when the eyes perceive motion, but the ear does not. Both of these situations will be described in more detail in conjunction with the attached drawings.

It is important to note that the directional haptic feedback provided by the device does not need to disrupt the mechanism of the vestibular system (which processes sensory information from the inner ear controlling balance). It is sufficient that the directional haptic feedback provides an additional, directional stimulus that is perceived by the body's natural sense of touch in addition to visual and vestibular cues. Attempting to disrupt the vestibular system (e.g., through vibrations at the temples or cheekbones attempting to cause vibrations in the inner ear) requires substantially more energy (an order of magnitude or more) than perceivable directional haptic feedback through tactile stimulation.

In an embodiment, the feedback is improved by adjusting the feedback to account for differences between two reference frames of motion: motion associated with the user's visual frame of reference (an internal frame of reference) and motion associated with the user's vestibular frame of reference (an external frame of reference). In this dual reference frame approach, the user may be in motion in an internal frame of reference, wherein the user is able to visually perceive his or her motion within that reference frame, but unable to perceive his or her motion in an external frame of reference. The user's motion within the internal frame of reference will not cause motion sickness because the user's visual perception of motion within the internal frame of reference matches the user's vestibular perception of motion within that frame of reference. However, where there is additional motion in an external frame of reference, that motion will be perceived by the user's vestibular system, but will not be visually perceptible to the user. Hence, the motion for which correction should be made is the difference between the motion in the internal frame of reference and the external frame of reference.

As an example, consider a person walking inside a hallway of a large ship. The person's perception of his or her motion within the hallway (an internal reference frame) will not cause motion sickness because the person's visual perception of his or her movement within the hallway matches the persons vestibular perception of his or her movement within the hallway. Therefore, no additional stimulus associated with movement within the hallway is needed to prevent motion sickness. However, as the ship itself is moving in terms of acceleration, deceleration, roll, pitch, and yaw (an external reference frame), the person within the hallway cannot perceive the ship's motion visually, but the person's vestibular system will perceive the ship's motion. Assume for a moment that the person starts walking toward the bow in the hallway while the ship is accelerating forward. If the person starts walking forward, if the person's own walking acceleration is not deducted from the ship's forward acceleration, the amount of stimulus needed to correct for motion sickness will be over-estimated as the combination of the person's forward acceleration and the ship's forward acceleration, when the stimulus only needs to be applied to correct for the ship's forward acceleration (which cannot be perceived visually by the person).

The person's motion within the internal frame of reference need not be measured by a sensor attached to the person. In some embodiments, the person's motion within the internal frame of reference can be measured by other sensors within the internal frame of reference such as cameras. While the internal frame of reference will frequently be an enclosed space such as the interior of an airplane or ship, the phrase is not so limited. The internal frame of reference need not be an enclosed space, but can be any location or situation in which the person is unable to perceive (or unable to fully perceive) a motion in a larger frame of reference. For example, the internal reference frame may be a person's walking on a floating dock while looking downward at the dock (such that the person cannot perceive the motion of the dock visually) and the external reference frame may be the motion of the dock itself.

Many different sensor and/or data configurations may be used to establish location and/or movement of either reference frame or of the relative differences in location and movement between the dual reference frames. Sensors attached to the person (e.g., in a headband) can be used to detect location and/or movement of the person and/or the internal reference frame. Alternately, the person's location and/or movement (or that of the internal reference frame) could be determined by external sensors or data (e.g., a camera pointed at the person). Likewise, sensors attached to some element of an external reference frame (e.g., sensors attached to a vehicle in which or on which the person is traveling) could be used to determine location and/or movement of the external reference frame. Alternately, the location and/or movement of the external reference frame could be determined by sensors on the person (e.g., a gyroscope that maintains the direction of the vehicle regardless of the person's movement), external sensors (e.g., a camera pointed at the vehicle), or external data feeds (e.g., a data feed from an aircraft tracking service such as FlightAware.).

In some embodiments, a reference sensor or reference data can be used to determine the relative locations or movements of the internal and external reference frames. For example, a magnetometer may detect a common orienting field such as the Earth's magnetic field or a gyroscope may be used to determine a fixed orientation, and the location and movement of sensors for the internal and external reference frames may be calculated based on the data from the magnetometer or gyroscope. The reference sensor may be within one of the reference frames or may be external to both reference frames. In some embodiments, a sensor used to detect location and movement of one reference frame can be used as the reference sensor. In some embodiments, one or more sensors may broadcast data to other sensors. In some embodiments, multiple sensors may be included in a single detection unit (for example, some integrated circuit (IC) sensors are manufactured with on-chip gyroscopes and accelerometers and on-chip algorithms for processing complex multi-axis motion calculations).

A single sensor can be configured to provide information about the internal reference frame, the external reference frame, or a combination of the two. For example, in at embodiment, algorithms for sensors embedded in a person's shoes could detect both steps of the person (indicating the person's movement within the internal reference frame) as well as non-step movement such as subtle, repeated shifting of weight between the feet (indicating movement of the external reference frame such as the rocking of a ship in which the person is standing).

In some embodiments, the motion sickness reduction device may comprise a "kit" of sensors that can be temporarily deployed on a reference frame. For example, such a kit might include a magnetic wall-mountable movement sensor which can be attached to a wall or other surface in the interior of a cruise ship cabin to act as a sensor for the external reference frame of the ship, while sensors attached to the person (e.g., in a headband) act as sensors for the internal reference frame associated with the person's movement within the cruise ship cabin.

While it is less common, in some circumstances it is possible that the user can perceive motion in the external frame of reference, but not within the internal frame of reference. Such a situation might occur, for example, if a person is walking inside a train while looking out of the window. The person visually perceives the motion of the train (the external frame of reference), but does not perceive his or her own motion within the internal frame of reference (the corridor of the train within which the person is walking). In such cases, the corrections from the difference between the internal and external frames may be reversed to prevent motion sickness, and the motion sickness prevention device may either have a manual switch to reverse the corrections, or may be provided with sensors and programming that automatically reverse the corrections (e.g., an accelerometer in a headband could detect a quick turn of the head to look to the side).

The external frame of reference will often be a vehicle of some sort, but is not so limited. The external frame of reference simply needs to be a larger reference frame that has motion relative to the internal frame of reference within which the user is located. For example, the internal reference frame may be a person's walking on a floating dock while looking downward at the dock (such that the person cannot perceive the motion of the dock visually) and the external reference frame may be the motion of the dock itself.

In some embodiments, the device may be used to enhance human sensory inputs by providing feedback regarding the direction and distance of objects. For example, in low light conditions or for individuals with vision impairment, the device may be configured to provide tactile stimulation in the direction of objects in the user's environment that may not be visible to the user. In some embodiments, the device may be configured to provide tactile feedback related other sensory enhancements, such the direction and magnitude of temperature sources, sound sources (especially, for example, those in the ultrasound or infrasound range), light sources outside of the human-visible spectrum, etc.

In some embodiments, the device may be used to improve existing neural rehabilitation routines by providing synchronized haptic and/or electrical simulation to specific regions of the brain for the targeted user movement or cognitive function. Using sensors and transducers that convert electrical signals to a tactile sensation such as pressure, vibration, electrical stimulation (including all types of waveform signal), temperature, or airflow, such synchronized haptic and/or electrical simulations for the targeted rehabilitation routines (such as bodily movement or cognitive functions) will improve the overall effectiveness of such rehabilitation routines. Such haptic and/or electrical simulations may be synchronized with the desired rehabilitation routines using transducers that convert electrical signals to a tactile sensation such as pressure, vibration, electrical stimulation (including all types of waveform signal), temperature, or airflow. The transducers are located on the head, covering the entire surface area of the brain. And these transducers will be synchronized with additional sensors or sensory controls (as in a 2D video game or Virtual Reality environment) located at specific locations on the body of a user for the targeted rehabilitation functions to improve the recovery of existing neural networks or the development of new, alternative neural networks around damaged neurons. For example, when a stroke patient with a severe left hemisphere brain damage practices right hand and eye movements (for a given rehabilitation routine), the device will stimulate both the posterior parietal cortex region (which is involved in transforming visual information into motor commands) and the central (hand) region of the primary motor cortex.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"Location" as used herein means the position or orientation, or a combination of these aspects, of a person or thing. Location may be absolute or relative to another thing.

"Movement" as used herein means a change in location of a person or thing. The change in location may be a change in position, direction, or orientation, or any combination of these aspects, and includes all derivative calculations of movement such as velocity, acceleration, jerk, jounce, etc.

"Transducer" as used herein means a device that is actuated by power from one system and supplies power usually in another form to a second system. Typically, this will mean conversion of electrical signals to kinetic energy (vibration or pressure), heat or cooling, electrical stimulation (same type of energy, but at a different frequency, amplitude, voltage, or current), sound, airflow, etc.

Conceptual Architecture

FIG. 1 is a diagram illustrating the causes of motion sickness, and illustrating how a third motion perception input may reduce motion sickness. On the right-hand side of the diagram as shown in 120, it is shown that motion sickness can occur when the inner ear correctly perceives motion 121, but the eyes incorrectly do not 122. This cause of motion sickness occurs frequently during real-world travel. For example, when a person is traveling inside the hull of a ship, the person visually perceives 122 that his surroundings are not moving because he is not moving relative to the interior of the ship. However, the inner ear correctly perceives 121 that the person's body is, in fact, moving, along with the entire ship. The brain receives signals indicating movement from the inner ear 121, but signals indicating no movement from the eyes 122. This conflict between the inertial perception of movement 121 and visual perception of stillness 122 causes motion sickness.

On the left-hand side of the diagram as shown in 110, motion sickness can occur when the eyes perceive motion 112, but the inner ear does not 111. This cause of motion sickness is most frequently found in artificial situations. For example, this type of motion sickness can be induced by having a person sit in a chair while artificial "walls" hung from above are rocked back and forth or rotated. Today, however, the most common cause of this type of motion sickness is virtual reality (VR) games, wherein the player perceives movement visually 112 on a screen inside of a VR headset, but the player's body is not moving 111 in the same way as the images on the screen. So, for example, the player might be visually perceiving 112 that he is in a car engaged in a high-speed chase through a city, but inertially perceiving 111 (correctly) that he is actually sitting on a couch in his living room. In this case, the brain receives signals indicating movement from the eyes 112, but signals indicating no movement from the inner ear 111. This conflict between the visual perception of movement 112 and inertial perception 111 of stillness causes motion sickness.

However, while visual and inertial cues are the primary signals used by the brain to process motion, the brain also receives movement signals from a third source, the somatosensory system, or tactile senses 113, 123. The brain is already "wired" to accept directional cues based on tactile sensation such as moving air. When moving forward one feels the rush of air coming from the front, confirming to the brain the sense received from the eyes and inner ear that we are moving forward. In many situations, the tactile sense can be a pressure against the body from acceleration, such as being pressed against the seat of a car during acceleration or turning. This tactile sense, which often confirms movement to the brain, can be used to confirm a sense of movement received from either the eyes or the inner ear, reducing the sense of non-movement from the other sense, thus providing the brain with an enhanced sense of movement from one sense and a diminished sense of lack of movement from another sense, thereby reducing the conflicting signals in the brain regarding movement and reducing motion sickness. The tactile perception of movement, then, acts as a sort of "tie-breaker" between the perceptions of movement and non-movement from the eyes and inner ear, enhancing the brain's perception of movement and diminishing the brain's sense of stillness.

For example, in the case of real-world motion sickness 120, there is an incorrect visual perception of stillness 122, and a correct inertial perception of movement 121. Normally, this conflict in perceptions would result in motion sickness. However, if a tactile indication of movement 123 is added through a haptic feedback device, the tactile indication of movement 123 enhances the brain's perception of movement from the inertial perception 121 from the inner ear, and diminishes (or masks) the visual perception of stillness 122 from the eyes. The result is that the brain senses less of a conflict between senses and is not prompted to induce nausea.

In the case of motion sickness induced by artificial environments such as VR gaming 110, there is an artificial visual perception of motion 112, for example from the screen inside a VR headset, and a real inertial perception of stillness 111. Normally, this conflict in perceptions would result in motion sickness. However, if a tactile indication of movement 113 is added through a haptic feedback device, the tactile indication of movement 113 enhances the brain's perception of movement from the artificial visual perception 112 from the eyes, and diminishes (or masks) the inertial perception of stillness 111 from the inner ear. Again, the result is that the brain senses less of a conflict between senses and is not prompted to induce nausea.

While the tactile input is of lesser importance when there is no conflict as to perception of motion, it becomes the deciding factor when there is such a conflict. The tactile sensation is sufficient to "trick" the brain into believing that the perceived motion is justified, and that there is no need for the brain to induce sickness.

Inducing a tactile perception of motion makes it possible to experience visually-perceived motion in a virtual reality environment that does not correspond to movements in the real world without experiencing motion sickness. In a VR environment, the tactile input is used to reinforce the vision to make the brain accept that the vision is showing the correct data and ignore the signals from the inner ear. As a side effect, it also improves the level of immersion in VR. Embodiments for VR motion sickness reduction could be used not only for gaming purposes, but for other virtual reality interactions such as three-dimensional walkthroughs of real estate, virtual visits to famous locations, or group virtual vacations with friends.

Likewise, inducing a tactile perception of motion makes it possible to reduce the effects of motion sickness when traveling in the real world where the inertially-perceived motion from the inner ear does not match the visual perceptions of stillness, as is the case when traveling inside a ship, for example. In another application for reducing vehicle-induced motion sickness (often called "car sickness" due to its common occurrence when riding in automobile), the tactile input is used to reinforce the inertial sensation and to ignore the visual signals. This is particularly useful where individuals in a vehicle are not driving or operating the vehicle, which is the scenario in which vehicle-induced motion sickness is mostly likely to occur. It should be noted that, in the case of self-driving (also called autonomous) vehicles, all individuals in the vehicle are passengers, and thus at greater risk of motion sickness.

Figure 6:
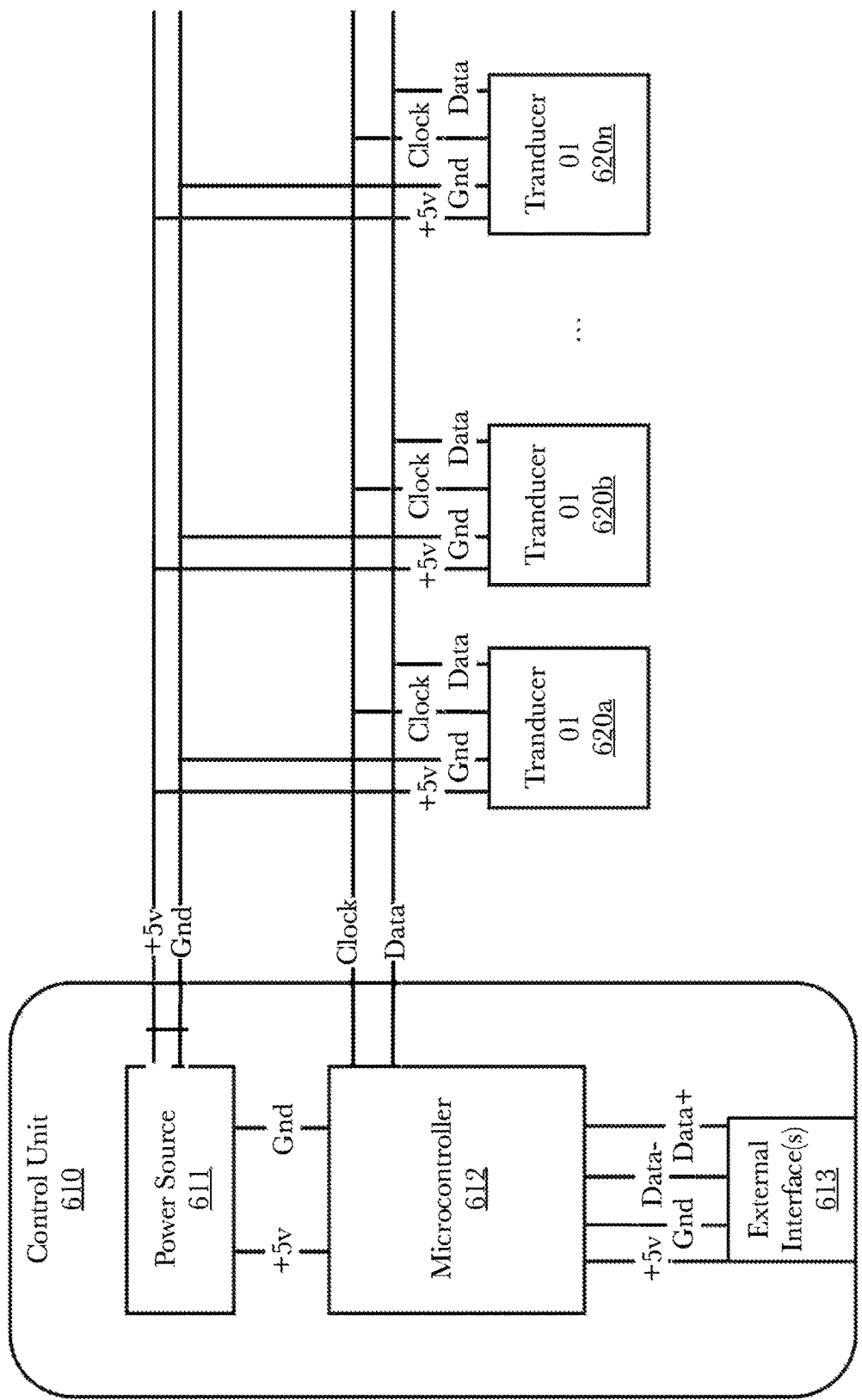
FIG. 6 is a diagram illustrating an exemplary control system architecture of an embodiment.

FIG. 6 is a diagram illustrating an exemplary control system architecture of an embodiment. A control unit 610 comprises a power source 611, a microcontroller 612, and an external interface 613. The control unit controls one or more independently-addressable transducers 620a-n. In this embodiment, the power source is batteries, but in other embodiments the power source 611 may be an alternating current/direct current (AC/DC) converter using power plugged in from an external AC source, or power may be supplied from an external DC source through a connector, or power may be supplied through the external interface 613. The external interface 613 is an interface capable of communicating with another electronic device. In this embodiment, a standard universal serial bus, Type A (USB-A) interface is shown with four wires corresponding to +5 volts, ground, data-, and data+. The microcontroller 612 is a small computing device with one or more processors, a memory, communications controllers, and one or more inputs and outputs. Microcontrollers in this type of application are typically pre-programmed for the intended use. The microcontroller 612 is used to receive input signals either from sensors or other computing devices, and operate the transducers 620a-n in accordance with the signals received. In this embodiment, the microcontroller 612 contains an inter-integrated circuit bus (such as I2C and SPI) bus which allows for fully-addressable serial communication with each transducer 620a-n, using common wires for +5 v and ground (for power), a clock signal, and data. Each transducer 620a-n also contains a communications controller allowing for I2C serial communications with the microcontroller 612. In this embodiment, signals pertaining to direction and magnitude of movement are received through the external interface 613, and the microcontroller 612 operates the transducers 620a-n corresponding to the direction relative to the user (e.g., at appropriate locations on a headband worn by the user), and adjusts the intensity of transducer 620a-n operation according to the magnitude signal. In other embodiments, direction and magnitude signals may be received from external sensors, or from sensors contained within the control unit 610 (e.g., accelerometers, gyroscopes, etc.). In some embodiments, additional signals or data may be received by the microcontroller 612 such as identification of objects or objectives, and the microcontroller 612 may adjust operation of the transducers 620a-n to indicate to the user differences between objects or objectives based on the identification. For example, the transducers 620a-n may be pulsed at different intervals based on the distance away from an objective, or operated at different intensities to indicate different threat levels of objects or entities. Although this example uses the I2C serial communications protocol, any addressable communication protocol may be used, including serial and parallel communications protocols. It should be noted that while fully-addressable transducers are used to reduce the amount of wiring, it is quite possible to directly wire each transducer rather than use serial communication protocols. In some embodiments, wireless communications between the microcontroller 612 and the transducers 620a-n (or between transducers 620a-n) may be used instead of wired communications.

A person of ordinary skill in the art will recognize that this configuration is simply one of many such configurations, and that the various components may be contained in, or distributed among, various other components and/or locations. For example, the computing device and the algorithms controlling the activations of the transducers may be located in the headband, in a control unit attached to or integrated into the headband, in a separate wired device attached to or plugged into the headband, or in a wireless device like a mobile phone, tablet, or desktop computer. In some embodiments, portions of the control system may be located on distributed computer systems (e.g., websites, cloud-based computing platforms, distributed networked server systems, etc.).

FIG. 7 is a diagram illustrating an exemplary method 700 for motion sickness reduction. As an initial step, input is obtained comprising a direction of motion and a magnitude of motion from a sensor or other device 701. Based on the input, one or more transducers in the direction of motion relative to the user are operated 702. The intensity of the operated transducers is then adjusted according to the magnitude of the input and/or the direction of the transducer versus the direction of motion 703. These steps are repeated continuously for as long as the user desires.

A use of the system may be in a moving vehicle such as a car, where many individuals may feel motion sickness to varying degrees. A headband-like device could be connected to a device with a gyroscope and accelerometer such as many smartphone devices, which may then inform the headband-like device of movements and accelerations the vehicle undergoes, and provide the user with additional tactile feedback in the direction of movement, to enhance the brain's digestion of bodily sensory data and reduce the possibility or severity of the nausea felt from receiving incorrect signals as shown in FIG. 1.

Figure 8:
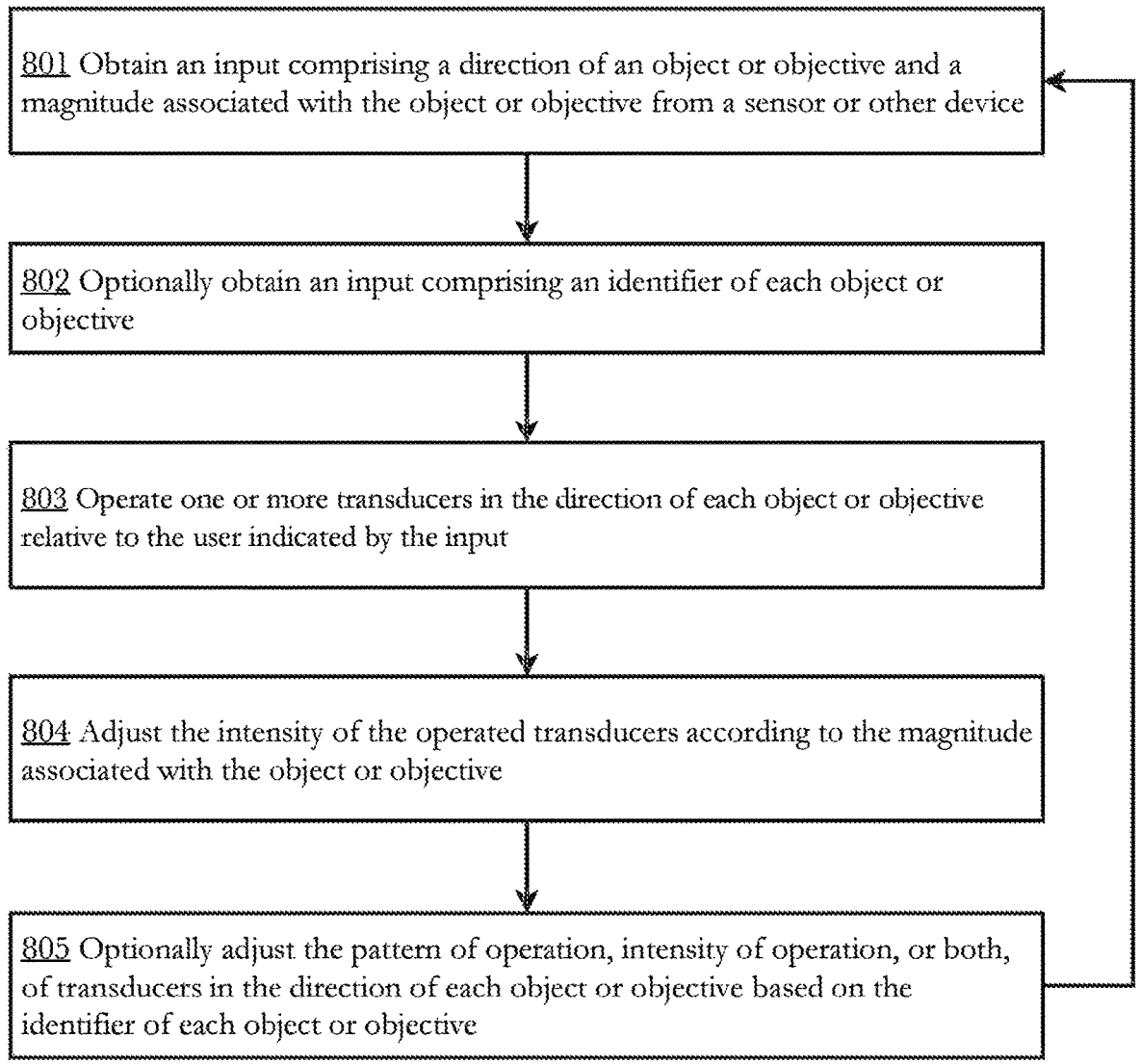
FIG. 8 is a diagram illustrating an exemplary method for directional indication.

FIG. 8 is a diagram illustrating an exemplary method 800 for directional indication. As an initial step, input is obtained comprising a direction of an object or objective and a magnitude associated with the object (or entity) or objective from a sensor or other device 801. Optionally, input may be obtained comprising an identifier of each object (or entity) or objective 802. Based on the input, one or more transducers in the direction of each object or objective relative to the user are operated 803. The intensity of the operated transducers is adjusted according to the magnitude input associated with the object or objective 804. If an identifier is used, the pattern of operation, intensity of operation, or both, of transducers in the direction of each object or objective may be adjusted based on the identifier of each object or objective 805. This sequence of steps may be repeated continuously.

For example, the system of this exemplary embodiment, depending on where it is located on a user and the extent of its body coverage, could be used in a virtual reality simulation wherein a user's character or avatar is walking in rain. The drops of the rain could be simulated with measured and programmed tactile feedback from the transducers, to cause the user to feel as though the user is in the rain.

A further use of the system in the field of virtual reality simulations may be for flight simulators, or driving simulators. A user may experience motion sickness due to the disconnect of the tactile or inertial feedback received, or lack thereof, compared to the visual simulation, which may be lessened by the use of a system such as a headband or other device which may produce tactile vibrations or other haptic feedback, such as with transducers, in a direction matching the direction of force as programmed in the simulation controlling the tactile feedback device. If a user turns a plane sharply left, the device may vibrate on the left side, to stimulate the user's tactile senses as they would feel if they had actually been in such an aircraft undertaking such a maneuver.

Figure 16:
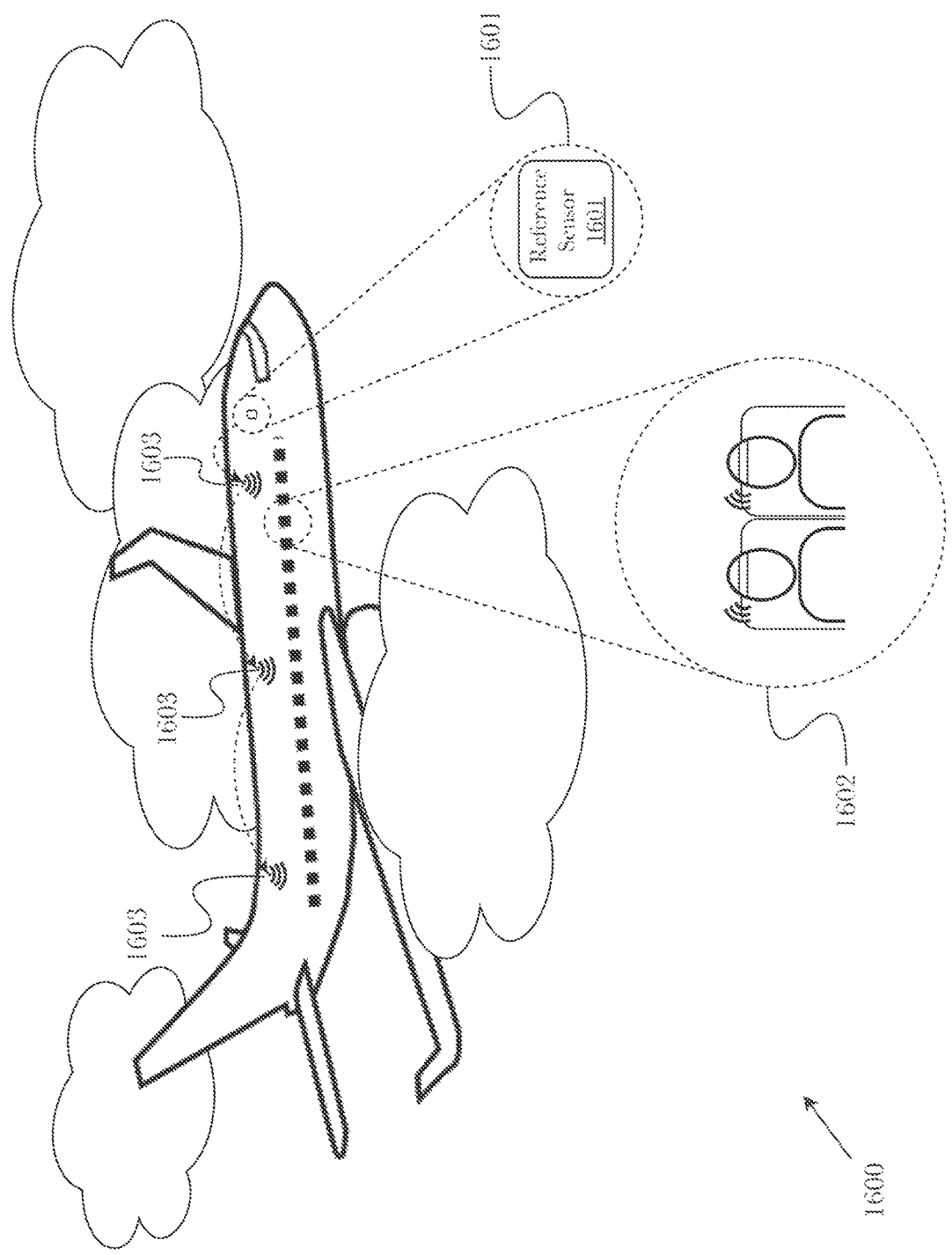
FIG. 16 is a diagram illustrating an exemplary embodiment of a device for motion sickness reduction and directional indication using external sensors on an aircraft.

FIG. 16 is a diagram illustrating an exemplary embodiment of a device for motion sickness reduction and directional indication using external reference frame sensors on an aircraft 1600. Passengers and crew 1602 aboard an aircraft may wear the headband described in previous figures with a sensor providing information about the internal reference frame (the person's position and movement within the interior of the aircraft), which is now communicatively coupled to an external reference frame sensor 1601 which provides information about the external reference frame (i.e., the aircraft's position and movement). In some embodiments, this external reference frame sensor 1601 may be affixed to the aircraft, but in other embodiments, other means may be used to establish the external reference frame of the aircraft. For example, a gyroscope could be used to establish the direction of the aircraft even if the gyroscope is affixed to the headband or otherwise attached to the person seeking to minimize motion sickness. In this way, whether a person is sitting, walking, or reading in the aircraft, the difference in movement between of the person and the aircraft is applied to the person's headband transducer, thus creating a tie-breaker between what the person sees and what his or her vestibular system reports.

According to one embodiment, one external sensor is used, and its data is repeated 1603 throughout the aircraft to be processed locally on each headband. According to another embodiment, multiple external reference frame sensors 1601 are deployed throughout the aircraft, each sensor 1601 broadcasting to a range of passenger headbands for local processing. According to other embodiments, one or more external reference frame sensors 1601 and each passenger headband sends their data to a central processing control unit and that control unit computes the proper headband stimulation for each headband and subsequently broadcasts back the pertinent data throughout the aircraft 1603 to each passenger.

Figure 17:
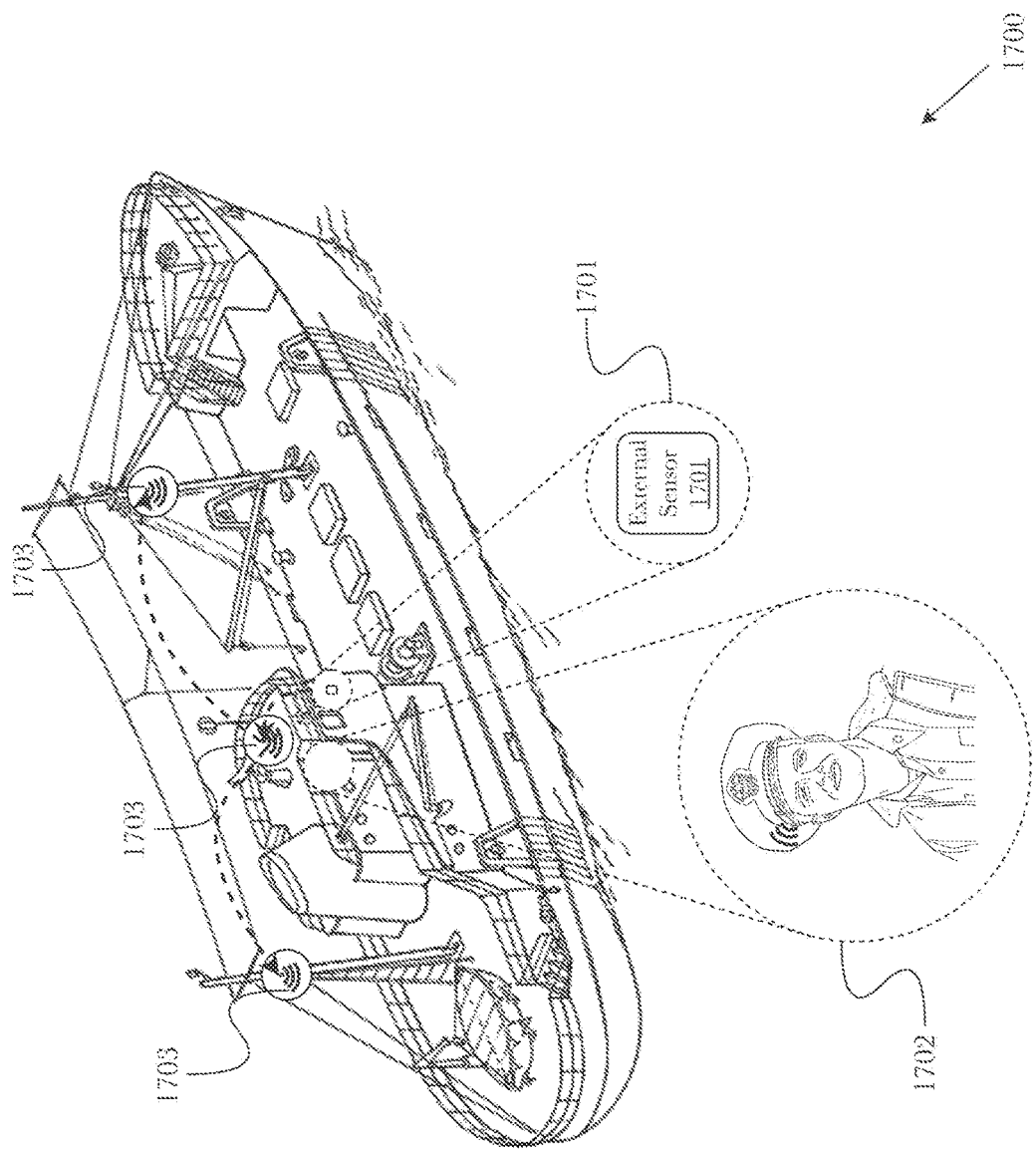
FIG. 17 is a diagram illustrating an exemplary embodiment of a device for motion sickness reduction and directional indication using external sensors on a ship.

FIG. 17 is a diagram illustrating an exemplary embodiment of a device for motion sickness reduction and directional indication using external reference frame sensors on a ship 1700. Passengers and crew 1702 aboard a ship, or any other watercraft, may wear the headband described in previous figures, which is now communicatively coupled to an external reference frame sensor 1701 which provides information about the external reference frame (i.e., the watercraft's position and movement). In some embodiments, this external reference frame sensor 1601 may be affixed to the watercraft, but in other embodiments, other means may be used to establish the external reference frame of the watercraft. For example, a gyroscope could be used to establish the direction of the watercraft even if the gyroscope is affixed to the headband or otherwise attached to the person seeking to minimize motion sickness. In this way, whether a person is sitting, walking, or reading in the watercraft, the difference in movement between of the person and the watercraft is applied to the person's headband transducer, thus creating a tie-breaker between what the person sees and what his or her vestibular system reports. According to one aspect, a headband 1702 may be integrated into a hat, such as a sailor's hat or pilot's helmet.

According to one embodiment, one external sensor is used, and its data is repeated 1703 throughout the watercraft to be processed locally on each headband. According to another embodiment, multiple external sensors 1701 are deployed throughout the watercraft, each sensor 1701 broadcasting to a range of passenger headbands for local processing. According to other embodiments, one or more external sensors 1701 and each passenger headband sends his or her data to a central processing control unit and that control unit computes the proper headband stimulation for each headband and subsequently broadcasts back the pertinent data throughout the watercraft 1703 to each passenger.

Figure 18:
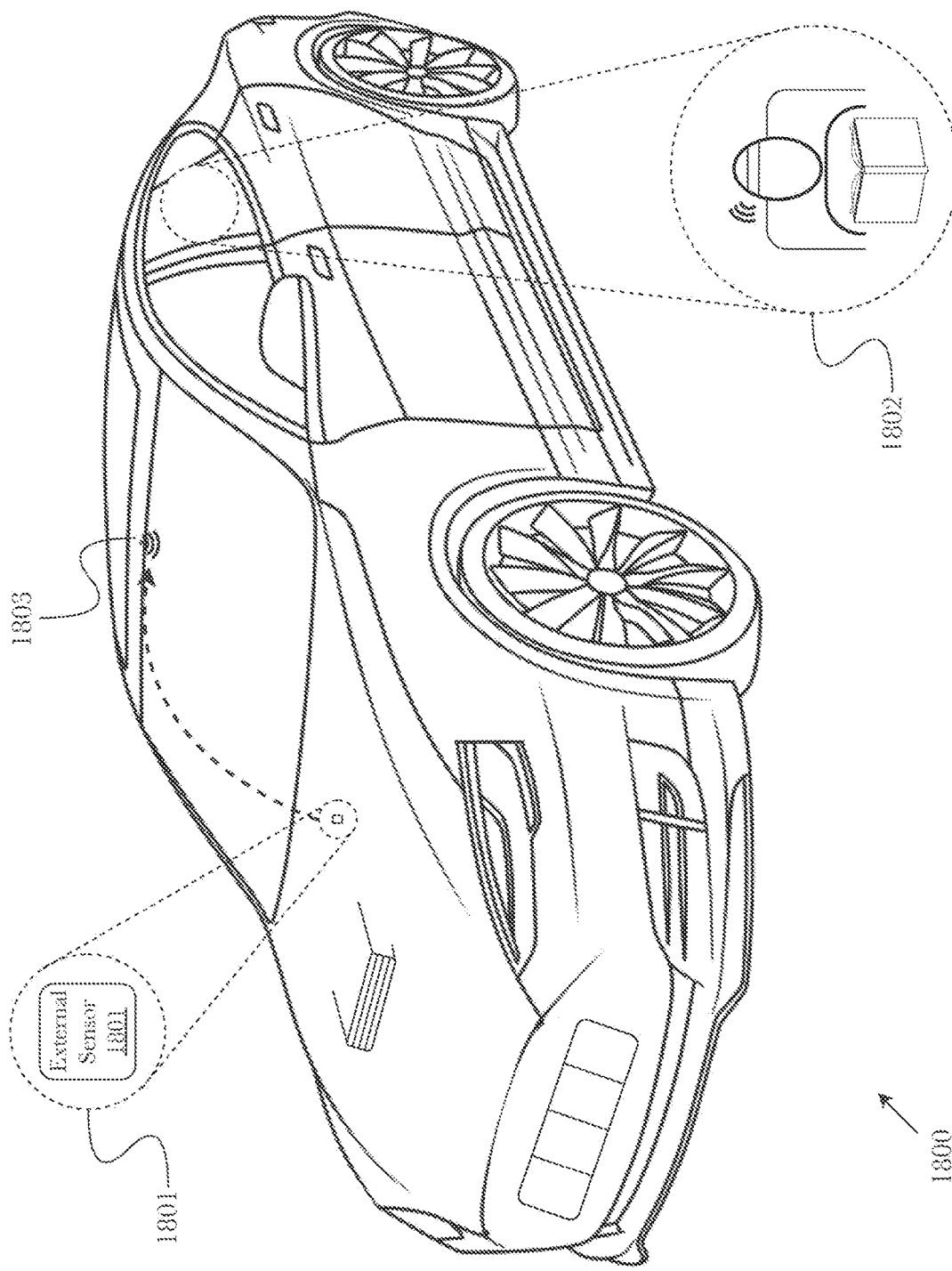
FIG. 18 is a diagram illustrating an exemplary embodiment of a device for motion sickness reduction and directional indication using external sensors on an automobile.

FIG. 18 is a diagram illustrating an exemplary embodiment of a device for motion sickness reduction and directional indication using external sensors on an automobile 1800. Passengers 1702 riding in an automobile, may wear the headband described in previous figures, which is now communicatively coupled to an external sensor 1801 which provides information about the external reference frame (i.e., the automobile's position and movement). In some embodiments, this external reference frame sensor 1601 may be affixed to the automobile, but in other embodiments, other means may be used to establish the external reference frame of the automobile. For example, a gyroscope could be used to establish the direction of the automobile even if the gyroscope is affixed to the headband or otherwise attached to the person seeking to minimize motion sickness. In this way, whether a person is reading, playing games, looking at an electronic device, or just experiencing motion sickness in general, the difference in movement between of the person and the automobile is applied to the person's headband transducer, thus creating a tie-breaker between what the person sees and what his or her vestibular system reports.

According to one embodiment, one external sensor is used, and its data is repeated 1803 throughout the automobile to be processed locally on each headband. According to another embodiment, multiple external sensors 1801 are deployed throughout the automobile, each sensor 1801 broadcasting to a range of passenger headbands for local processing. According to other embodiments, one or more external sensors 1801 and each passenger headband sends their data to a central processing control unit and that control unit computes the proper headband stimulation for each headband and subsequently broadcasts back the pertinent data throughout the automobile 1803 to each passenger. Embodiments comprising multiple sensors 1801 or multiple repeaters 1803 are intended for, but not limited to large passenger vehicles such as a bus or recreational vehicle.

Figure 19:
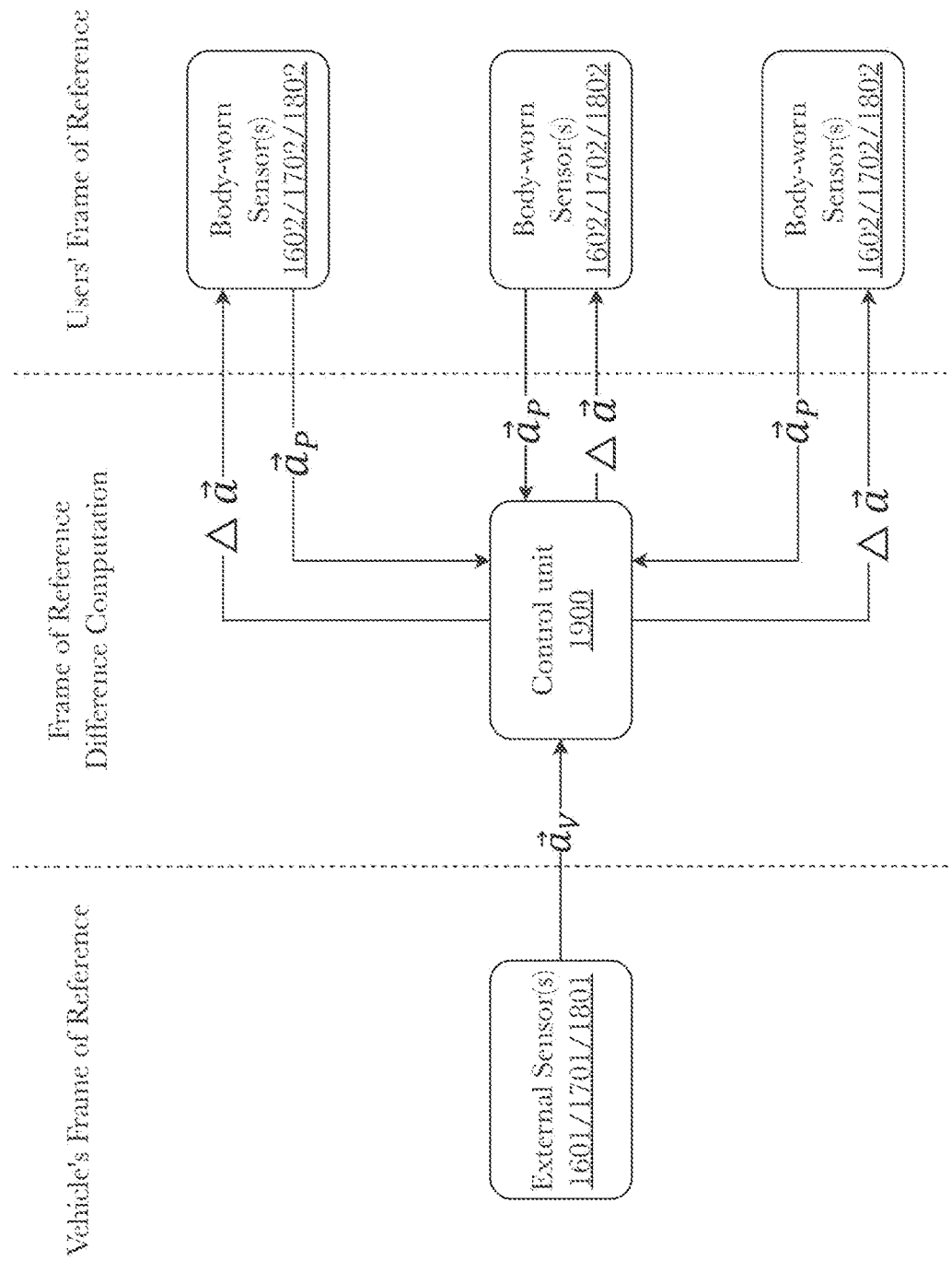
FIG. 19 is a block diagram illustrating exemplary system components for a motion sickness reduction device.

FIG. 19 is a block diagram illustrating exemplary system components for a motion sickness reduction device. An external sensor or a plurality of sensors 1601/1701/1801 measure the acceleration of a vehicle, denoted as $\vec{a}_V$. A headband controller or a device connected to the headband and on the body of the headband wearer—e.g., smartphone, 1602/1702/1802 measures the headband wearer's acceleration, denoted as $\vec{a}_P$. The measurements $\vec{a}_V$ and all $\vec{a}_P$s are sent to a control unit 1900. The control unit 1900 may be software running on the headband, a device (e.g., smartphone) connected to the headband, a computer on-board the vehicle, or a service based in the cloud. The control unit 1900 determines a difference between the vehicle's motion $\vec{a}_V$ and the person's motion $\vec{a}_P$, denoted as $\Delta\vec{a}$. The computation result $\Delta\vec{a}$ is then sent to each headband from which the headband will activate the appropriate transducers.

Here, the headband feedback is improved by adjusting the feedback to account for differences between two reference frames of motion, motion associated with the user's visual frame of reference (an internal frame of reference) and motion associated with the user's vestibular frame of reference (an external frame of reference). In this dual reference frame approach, the user may be in motion in an internal frame of reference, wherein the user is able to visually perceive his or her motion within that reference frame, but unable to perceive his or her motion in an external frame of reference. The user's motion within the internal frame of reference will not cause motion sickness because the user's visual perception of motion within the internal frame of reference matches the user's vestibular perception of motion within that frame of reference. However, where there is additional motion in an external frame of reference, that motion will be perceived by the user's vestibular system, but will not be visually perceptible to the user. Hence, the motion for which correction should be made is the difference between the motion in the internal frame of reference and the external frame of reference.

In each case where the headband wearer does not visually see the motion from the vehicles frame of reference, e.g., inside an aircraft, hull of a ship, looking down in a car, etc., the headband wearer's vestibular system will sense the vehicles motion and thus create the conflict. Therefore, the computation result $\Delta\vec{a}$ is the difference in motion between the user and the vehicle. In most cases, but not all, the vehicle is experiencing more acceleration and therefore the computation result $\Delta\vec{a}$ is composed of the vehicles motion that the user's vestibular system experiences but that is not experienced by the user's visual system. When the computation result $\Delta\vec{a}$ is applied to the headband, it acts as a tie-breaker to resolve the conflict. In some embodiments, the motion sickness reduction corrections may be based on some relationship between the two vectors other than a difference (e.g., averages, scalar multiples of the vector magnitudes, ratios, etc.) or relationships between the two vectors with one or more other vectors.

In some embodiments, the above calculations may be made on a change in a single vector (e.g., from a change in a single sensor) instead of a difference between two vectors (e.g., from the difference between two sensors). As an example, if a person is walking forward at a steady pace, and there is a sudden step change or rapid increase in the acceleration measured by a single sensor, the step change or rapid acceleration could be assumed to be movement of a vehicle, and the difference could be taken between the sensor values before the step change or rapid acceleration and after.

The embodiments above and elsewhere herein that make use of acceleration are not limited to using only acceleration. Other sensors, software, and integration and derivative circuits may be used to determine position, speed, velocity, acceleration, jerk, of both the vehicle and a person. Computation of the measurement difference may be performed on the headband, a device connected to the headband (e.g., a smartphone), on-premises (e.g., an aircraft's or ship's computer), or in the cloud.

Detailed Description of Exemplary Aspects

FIG. 2 is a diagram illustrating an exemplary embodiment 200 of a device for motion sickness reduction and directional indication. In this embodiment, the tactile sense indicator of movement is generated through a headband 201 comprising a controller 203 and a plurality of transducers 202 (in this case vibrating button motors as are commonly found inside mobile phones) placed equidistantly about the headband, such that the motors are distributed in a full circle around the top of the head when the headband is worn. The controller may also have interfaces 204 such as universal serial bus (USB) ports for connection to external devices. The controller 203 may be self-contained, containing batteries and acquiring inputs from accelerometers, gyroscopes, or other sensors in the controller 203, and operating the transducers 202 in response. Used in this way, the embodiment 200 may be used to combat motion sickness caused by real-world events such as traveling inside a ship, wherein the sensors inside the controller detect inertial motion, and direct the transducers 202 to provide a tactile indication of that motion to the user. Alternatively, the device may be connected through one or more interfaces 204 to external devices such as computers, VR headsets, etc., for use in combatting motion sickness induced through artificial environments such as VR games. Used in this way, the embodiment 200 may receive either power, or signals, or both from an external device, and the controller may use the signals received from the external device to control the operation of the transducers 202.

It should be noted that most types of transducers that would be used (e.g., pressure, vibration, electrical stimulation, temperature, airflow) would further be adjustable in terms of additional parameters such as time of operation, periodicity (frequency) of operation, and intensity (amplitude) of operation, allowing for adjustment of these parameters to provide the best motion sickness reducing effect. In some embodiments, parameters may be adjusted manually or automatically using scripts or algorithms. In some embodiments, parameters may be adjusted to suit particular users. In other embodiments, parameters of operation may be adjusted based on the intensity of motion (real or virtual) experienced.

Further, other embodiments may include transducers located at different locations on the body. While the headband encircling the top of the head is convenient for indicating horizontal directions relative to the head, other embodiments may place transducers around other parts of the body, such as the torso, arms, or legs. The invention is not limited to circular embodiments, however, and other embodiments may have transducers located only at strategic body locations (for example, the top of the head indicating upward movement or the bottom of the feet indicating downward movement). Some embodiments may feature wearable components fitted with transducers such as vests, jackets, arm bands or sleeves, leg bands or sleeves, or even full-body suits. Such embodiments would provide partial-body or full-body movement sensations.

Figure 3:
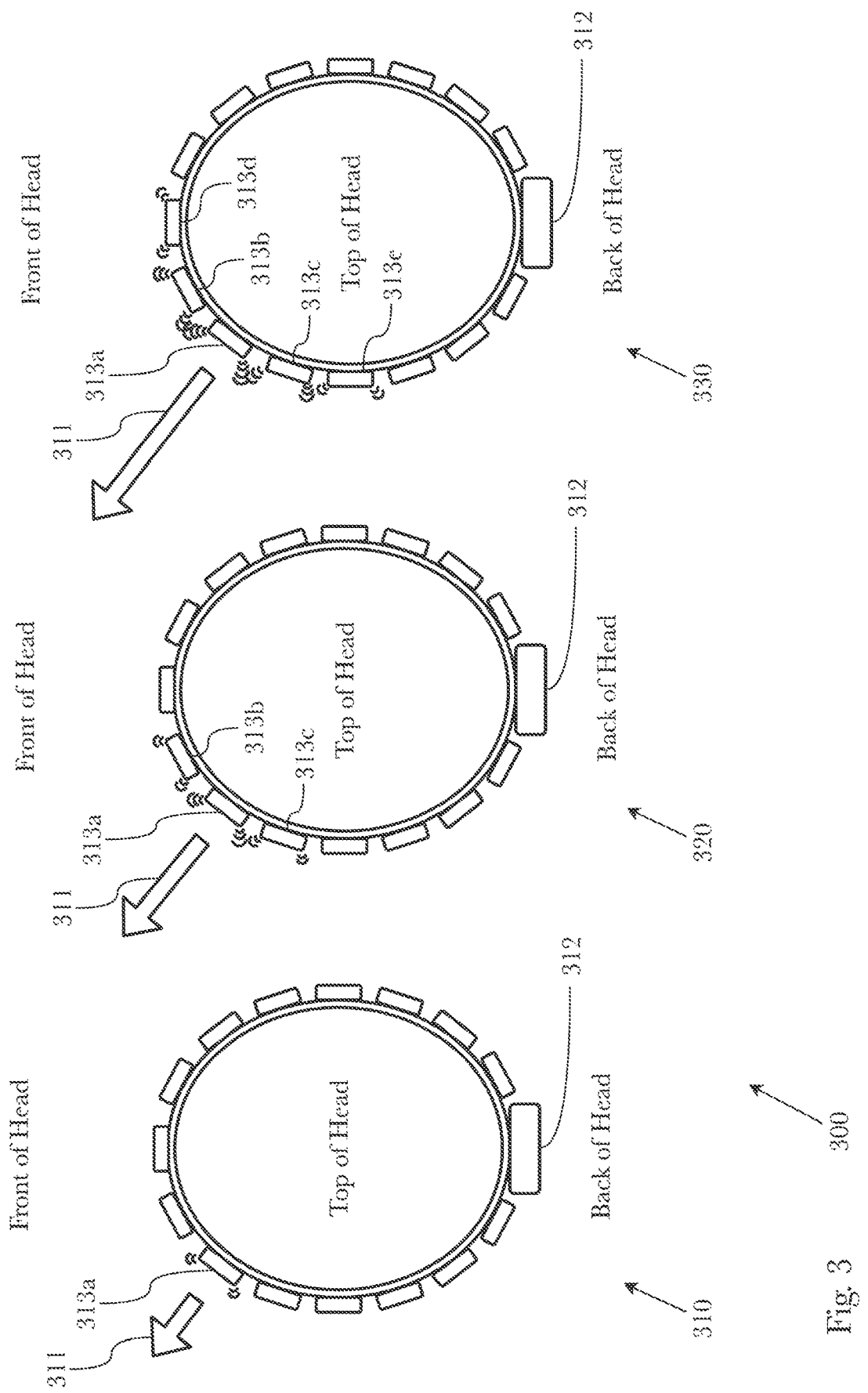
FIG. 3 is a diagram illustrating the operation of an exemplary embodiment to indicate a direction and magnitude of linear motion and/or acceleration.

FIG. 3 is a diagram illustrating the operation of an exemplary embodiment 300 to indicate a direction and magnitude of linear motion and/or acceleration. The operation of this exemplary embodiment 300 will be the same whether the device is used to provide tactile indication of real movement of the user (such as movement of a ship) or artificial visual movement of the user (such as in VR gaming). As shown in 310, as a user of the device starts to "move" (again, either actually or virtually) linearly in a given direction 311, the controller 312 activates the transducer closest in direction to the direction of movement 313a at a low level, providing the user with a tactile indication that the user is moving in the direction of movement 311 at a slow speed. As shown in 320, as the user gains speed in the same direction of movement 311, the controller 312 activates the transducer closest in direction to the direction of movement 313a with greater intensity, while simultaneously activating nearby transducers 313b, 313c at a low level, providing the user with a tactile indication that the user is moving in the direction of movement 311 at a moderate speed. As shown in 330, as the user gains further speed in the same direction of movement 311, the controller 312 activates the transducer closest in direction to the direction of movement 313a with the highest intensity, while simultaneously activating nearby transducers 313b, 313c at a moderate intensity level, and further adjacent transducers 313d, 313e at a low intensity, providing the user with a tactile indication that the user is moving in the direction of movement 311 at a fast speed. Thus, the tactile indications of movement can be adjusted in both direction and intensity to provide the user with a varying sensation of speed of movement and direction. In some embodiments, vertical motion may be represented by operation of some or all of the transducers simultaneously. For example, if the user jumps up and down, all of the transducers could be operated at the same time and intensity either as the user jumps, or lands, or both. While this example uses speed of motion as the magnitude of motion, it is also possible to use acceleration (including acceleration due to gravity) as the magnitude of motion, either as a substitute for speed or in conjunction with speed.

Figure 4:
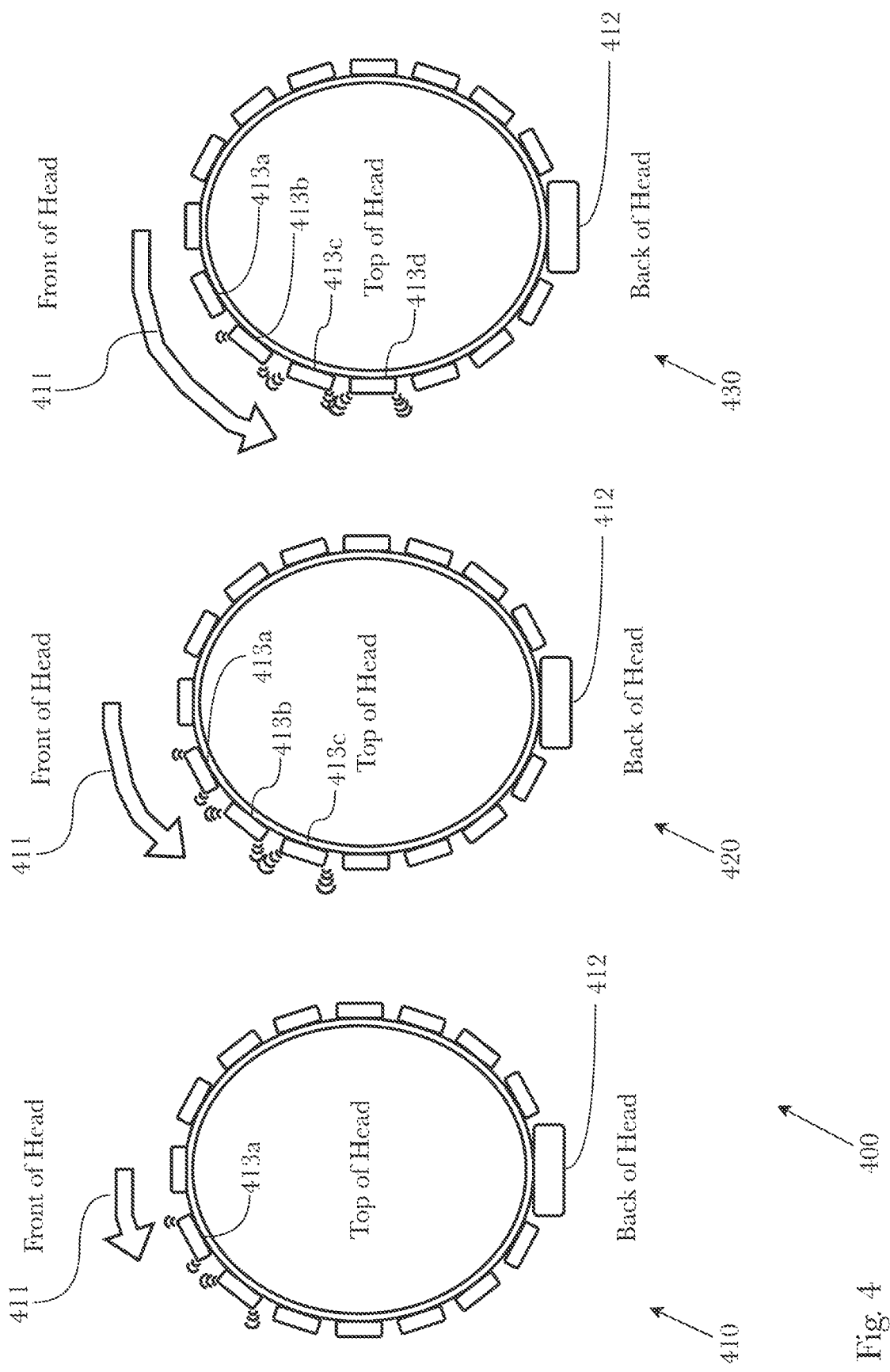
FIG. 4 is a diagram illustrating the operation of an exemplary embodiment to indicate a direction and magnitude of rotation.

FIG. 4 is a diagram illustrating the operation of an exemplary embodiment 400 to indicate a direction and speed of rotation. The operation of this exemplary embodiment 400 will be the same whether the device is used to provide tactile indication of real movement of the user (such as turning of a car) or artificial visual movement of the user (such as turning around in VR gaming). As shown in 410, as a user of the device starts to "rotate" (again, either actually or virtually) leftward 411, the controller 412 activates a transducers to the front of the head and off to the left side 413a at a low intensity, providing the user with a tactile indication that the user is rotating leftward 411 at a slow speed. As shown in 420, as the user gains speed in the leftward rotation 411, the controller 412 activates additional transducers on the left side further from the front of the head 413b, 413c with the transducers gaining in intensity in the direction of rotation, while simultaneously keeping the initial transducer 413a activated at a low level, providing the user with a tactile indication that the user is rotating leftward 411 at a moderate speed. As shown in 430, as the user gains further speed in the leftward rotation 411, the controller 412 activates the transducer furthest to the left at a high intensity 413d, while simultaneously keeping the transducers 413b, 413c activated and turning off transducer 413a, providing the user with a tactile indication that the user is moving in the direction of movement 411 at a fast speed. Taken as a sequence of events, the tactile indication intensifies as the speed of rotation increases and trails off toward the front of the head while intensifying at the left side of the head, thus creating a dynamic sense of rotation. The tactile indications of rotation can be adjusted in both direction and intensity to provide the user with a varying sensation of rotation speed and direction. While this example uses speed of motion as the magnitude of motion, it is also possible to use acceleration (including acceleration due to gravity) as the magnitude of motion, either as a substitute for speed or in conjunction with speed.

While speed is primarily used in the examples in FIG. 3 and FIG. 4, the accelerometers, gyroscopes, or other sensors in the controller 203, may capture any combination of positional data (e.g., GPS, distance sensors, proximity sensors, etc.), velocity data, or acceleration data. This applies for all embodiments of a controller, regardless of figure. Changes in one type of collected data may be used to derive other types of motion data. For example, changes in the positional data may be used to determine the speed, velocity, and acceleration. Likewise, integration on acceleration data can be used to determine speed, velocity, and positional data. According to some embodiments that desire GPS coordinates, the size of the controller can be reduced by tethering with an external GPS puck or a wearer's smartphone. Some embodiments may only use one motion sensor, such as an accelerometer, while other embodiments make use of multiple sensors—depending on the application.

Figure 5:
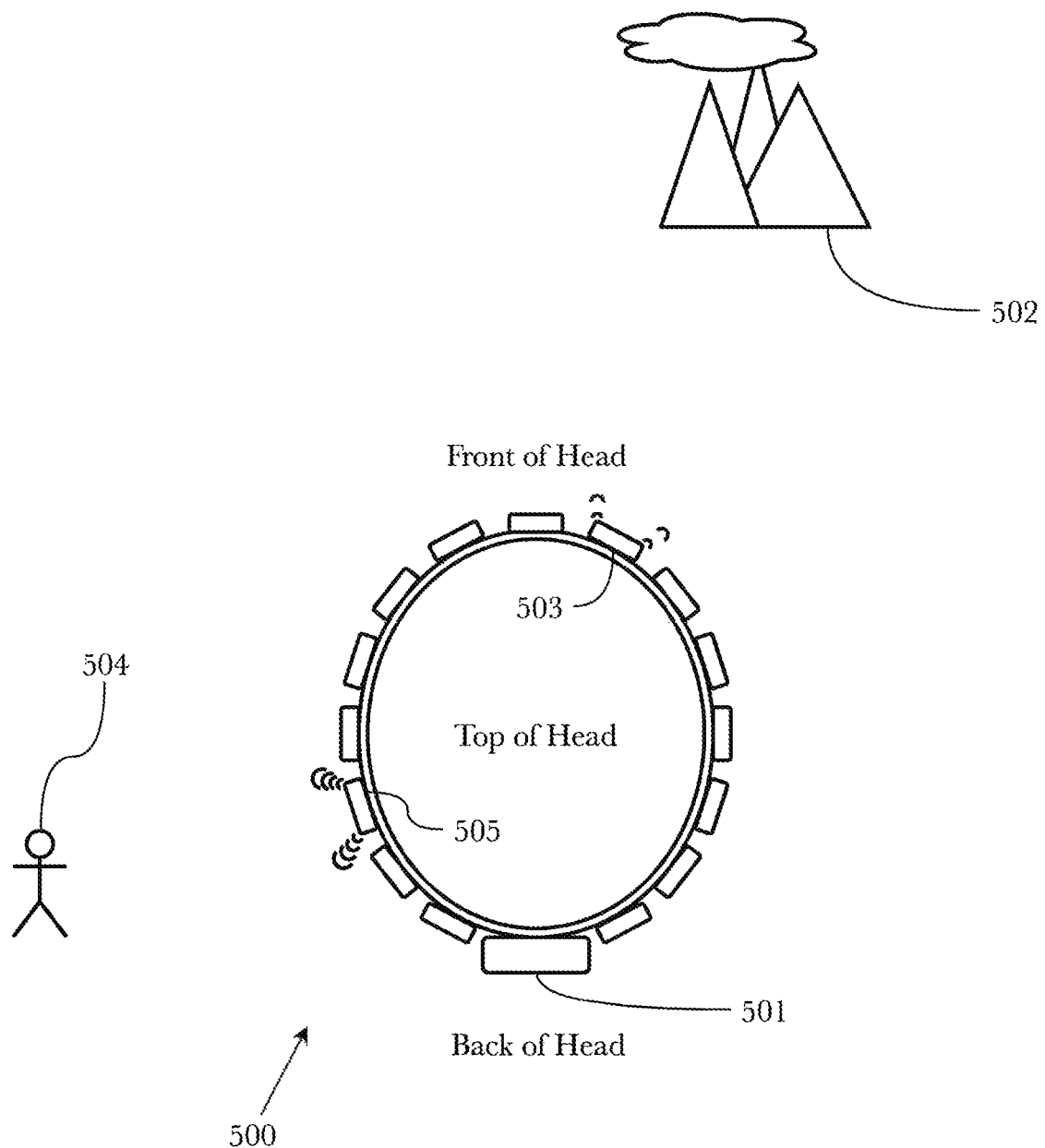
FIG. 5 is a diagram illustrating the operation of an exemplary embodiment to indicate a direction and distance of objects and objectives.

FIG. 5 is a diagram illustrating the operation of an exemplary embodiment 500 to indicate a direction and distance of objects and objectives. In this embodiment, signals may be sent to a controller 501, which operates certain transducers to indicate direction, distance, and even the type of object 504 or objective 502. For example, assume that the user is traveling toward an objective 502, in this case, a set of mountains in the distance. Signals may be sent to the controller 501 to indicate the direction and distance of the objective 502, and the controller 501 operates a transducer closest to the direction of the objective 503 in a pulsing manner. The location of the transducer 503 on the head indicates the direction of the objective 502, and the frequency and intensity of pulsing of the transducer 503 indicates the distance the user is away from the objective 502. For example, more frequent and more intense pulses might indicate that the user is getting closer to the objective 502. Simultaneously, other signals may be sent to the controller 501 indicating the direction of an object 504, in this case a person. The controller 501 would again operate the transducer closest in direction to the direction of the object 505. However, in this case, the controller 501 may operate the transducer 505 without pulsing, varying the intensity of the operation depending on one or more parameters associated with the object 504 (e.g., the closeness of the object, or the level of threat presented by the object). In some embodiments, sound may be used as additional feedback. For example, in addition to haptic (tactile) feedback, stereo sound could be used to enhance the directional guidance.

There are numerous ways in which an embodiment indicating direction and distance 500 could be used. For example, embodiments of this type may be used as warning indicators for people walking while using their mobile devices. Such people are likely to be distracted by looking at the mobile device screen and possibly also by listening to the mobile device with headphones, and are likely to be unaware of obstacles such as streetlights or dangers such as oncoming vehicles. Sensors either on the embodiment or on the mobile device may be used to detect such obstacles and dangers, and may warn the user of the direction and level of danger (e.g., speed of approach) posed. In military scenarios and military VR gaming analogs (i.e., first person perspective combat games, commonly known as first person shooters), such an embodiment could indicate the direction and number of potentially hostile actors, the direction of incoming fire, or the like.

In some embodiments, the device may be used to assist persons with visual impairments to navigate their environments. For example, the device may be paired with ultrasound-based distance sensors to identify the direction of, and distance of, objects nearby the user. The closer each object is to the user, the stronger the tactile feedback of the device could be in the direction of that object. Such a system would allow a vision-impaired user to avoid unexpected obstacles such as open doors or recently-moved furniture.

In some embodiments, additional sensors may be used to expand the sensory capabilities of the user. For example, ultrasound or infrared sensors could be used to detect the direction and location of objects in low-light environments. Temperature sensors could be used to detect the direction and magnitude of heat sources, and in some embodiments, could be used to identify the source of the heat. For example, a thermal imaging device could be used to the identify people by identifying heat sources with a temperature approximating normal human body temperature (typically 37° centigrade or 98.6° Fahrenheit). The distance of the person could be calculated by determining the pixel area occupied by the person's body in the thermal image, and that distance could be transmitted to the user of the device through tactile feedback.

Figure 9:
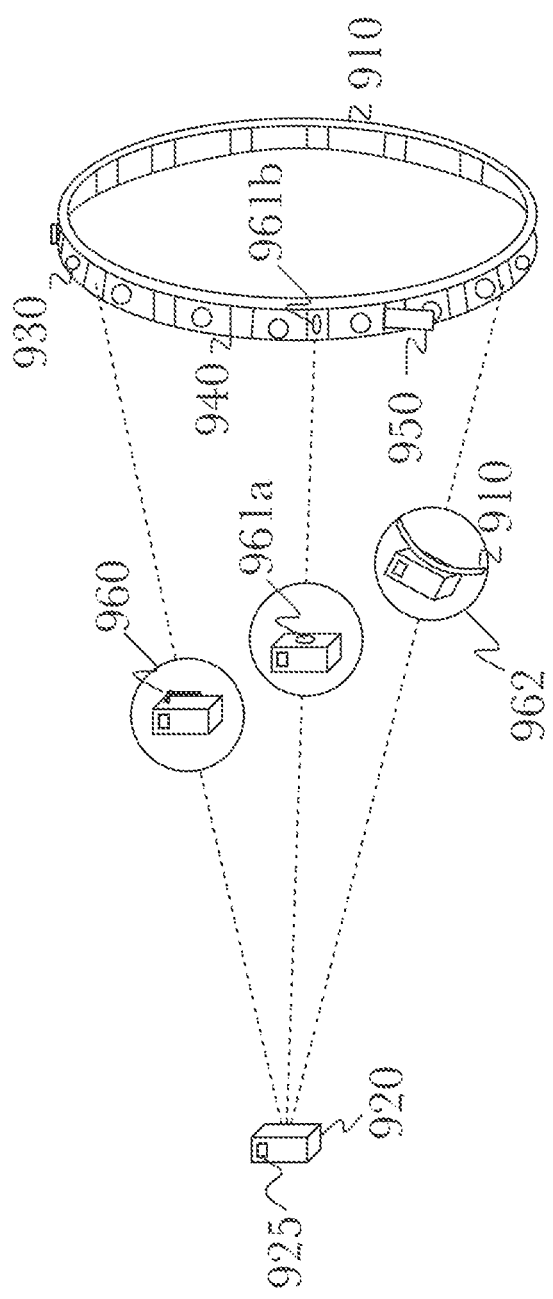
FIG. 9 is a diagram illustrating an exemplary embodiment of a device for motion sickness reduction and directional indication that may be placed on an arm or leg.

FIG. 9 is a diagram illustrating an exemplary embodiment of a device for motion sickness reduction and directional indication that may be placed on the arms, legs, torso, waist, neck, or any other part of the body about which a belt or strap may be affixed. Multiple devices may be attached to a plurality of body parts. A belt, strap, harness, or similar 910, exists as the basis for an extremity-based device for the reduction of motion sickness and for directional indication for such uses as virtual reality applications including virtual reality enabled video games. Such a belt, strap, harness, or similarly constructed object 910 may be placed individually on any extremity including either leg or either arm of a potential customer, separately or in tandem with other such straps or different straps such as a head-strap, head-covering, or similar. Materials that may construct such a device include cloth, cotton, linen, synthetic materials, or other appropriate materials for a strap-like device to be placed on an extremity. The belt may have placed on it, in it, or attached to it in some fashion, a controller 920 device, that may control or communicate with a device such as a personal computer, the function of the strap-like device 910. The controller 920 may house an interface 925 such as a universal serial bus ("USB") connection of any known or appropriate types such as type-A, type-B, or type-C, or some other wire connection if appropriate, according to the exemplary embodiment. It is possible for the device to also operate over wireless networking technologies such as BLUETOOTH™ rather than rely on a wired connection. A wired or wireless controller 920 may have one or a multiple of attachments points on the belt, strap, harness, or similar 910, such as between each transducer 930. The controller 920 may be attached to the belt, strap, harness, or similar 910 via a clip 960 that slides over the belt, strap, harness, or similar 910. The controller 920 may be attached to the belt, strap, harness, or similar 910 via a snap button, magnet, hook and loop fastener, etc. 961*a-b*. The controller 920 may be attached to the belt, strap, harness, or similar 910 via another attachment material or method not listed here. The controller 920 may also be permanently attached 962 to the belt, strap, harness, or similar 910. The belt, strap, harness, or similar 910 may have a length of communication wire for moving a wired controller 920 to different positions, the wire being secured or constructed in such a way as to not impede the function of the device.

The belt, strap, harness, or similar 910 has on it a series of transducers 930 that convert electrical signals to a tactile sensation such as pressure, vibration, electrical stimulation, temperature, or airflow, either equidistant from each other or spaced according to a specification other than equidistance. The harness, strap, attachment or other 910 is also, notably, constructed of a stretching or adjustable material or construction 940, such as an elastic material, or a rigid material that is designed for tightening and loosening, with the use of a tightening and loosening device such as a pull-tab 950. In this way, a device 910 may be tightened to different sizes of extremities across different users as desired, but also need not be adjusted if not needed. It is also possible for the device to have a button, strap, or other segment, where the device may disconnect from itself and become a linear strip, and may be attached again to allow for fitting around an extremity, much like a shirt with buttons or a bracelet with a clasp may be unclasped or unbuttoned, put on, and then buttoned or clasped again. Other possible fitting methods may be employed as well or instead of this or the pull-tab 950 method provided. This system may further be used to reduce motion sickness in a moving vehicle or similar, rather than in only a video game, regardless of whether or not a virtual reality simulation is being executed. The device does not require connection specifically to a virtual reality simulation to operate, but merely connection to a controlling device such as a phone with a controller application, a personal computer, or some other controlling device.

Such a device may be useful for the purposes of direction-based movement aiding to help remediate or reduce the effects of motion sickness and provide directional indication by potentially communicating with a controlling device such as a personal computer, an application on a mobile device, or some other controlling device, to provide physical sensation in accordance with the directions given by the controlling device. For example, a user may play a virtual reality game requiring frequent turning by the user. If this device were placed on a user's legs (requiring two such devices, one for each leg, which may work separately or in tandem according to the controller's software and game design), and a user turned to his or her left, the device may produce a tactile sensation to give him or her the sensation of air or wind brushing up against the left side of his or her left leg, to indicate turning into a breeze. In this way, the virtual reality experience provided may be enhanced, to help reduce the effects of motion sickness, and provide tactile sensations for directional movement and orientation, according to some embodiments. Other similar designs for directional movement being translated into tactile sensations may be utilized, as needed, and configuration settings in such controllers or applications may be able to account for such devices being mounted in differing configurations, orientations, or on different extremities or parts of the body.

Figure 10:
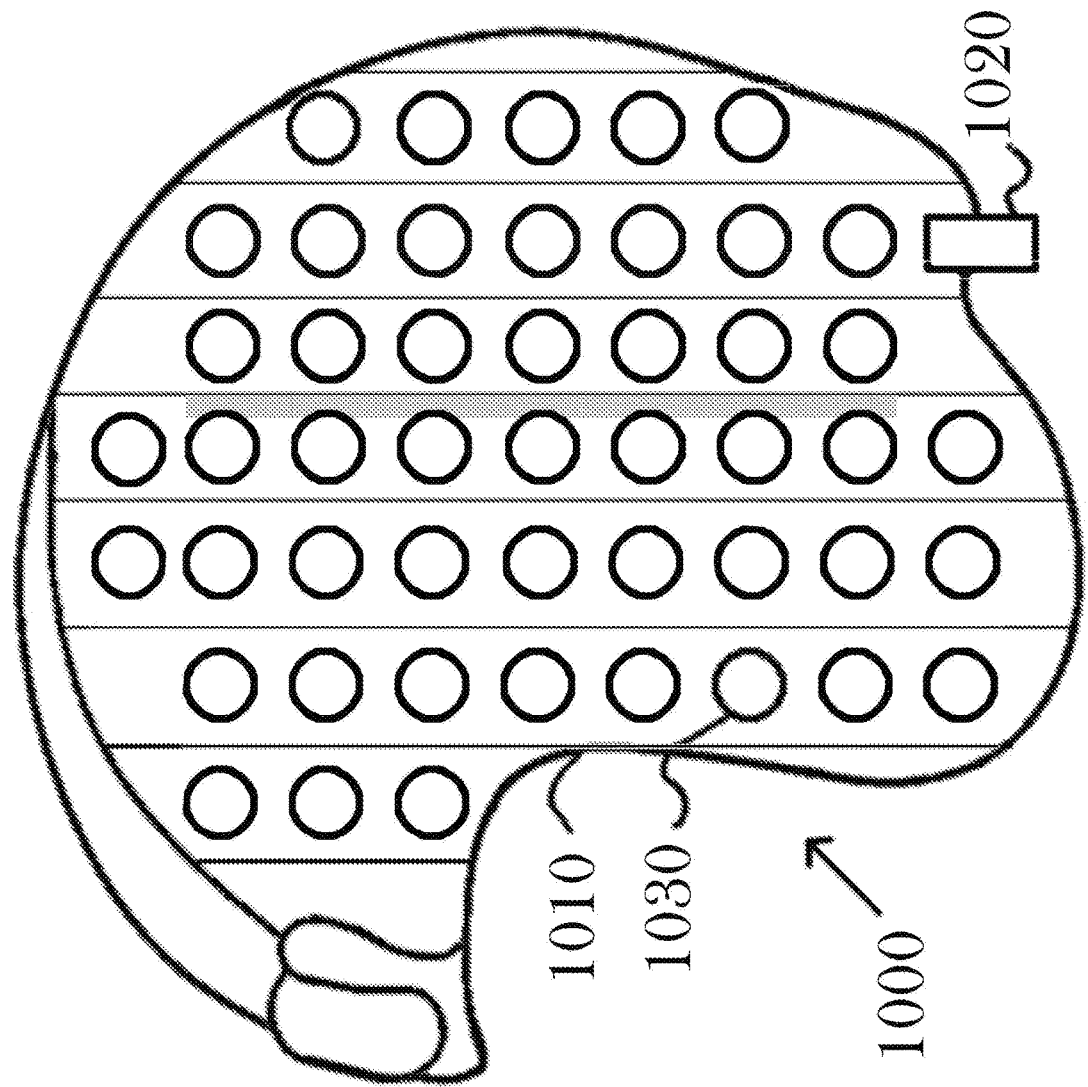
FIG. 10 is a diagram illustrating an exemplary embodiment of a device for motion sickness reduction, directional indication, and neural rehabilitation covering the entire head.

FIG. 10 is a diagram illustrating an exemplary embodiment of a device for motion sickness reduction and directional indication that may cover the entire head. A helmet, balaclava, or other head-covering mask or apparatus 1000 may exist, which may be constructed of a single or variety of materials including metals, organic materials such as cotton or others, synthetic materials such as plastics, or any processed and worked variants of these materials, such as refined linen or copper threads for conduction of electricity for its operation. The construction of the helmet, mesh, balaclava, or head covering does not cover the eyes or mouth 1010, allowing a user to comfortably wear the device, which may be made of a stretchable material for increased comfort, or the device may be available in multiple pre-determined sizes for a variety of consumers, among other possible solutions. The mask or covering is covered in transducers 1030, with the lines of the diagram showing only a possible relative alignment of such transducers, the actual specific alignment of the transducers being unimportant, the transducers 1030 merely being placed in an effective manner around the head-covering apparatus 1000. A connectivity plug 1020 is provided such as a universal serial bus ("USB") connection of any known or appropriate types such as type-A, type-B, or type-C, or some other wire connection if appropriate, according to the exemplary embodiment. It is possible for the device to also operate over wireless networking technologies such as BLUETOOTH™ rather than rely on a wired connection. The connection, whether wired or wireless, may be utilized to control the transducers' operation. This system may further be used to reduce motion sickness in a moving vehicle or similar, rather than in only a video game, regardless of whether or not a virtual reality simulation is being executed. The device does not require connection specifically to a virtual reality simulation to operate, but merely connection to a controlling device such as a phone with a controller application, a personal computer, or some other controlling device.

Such a device may be useful for the purposes of direction-based movement aiding to help remediate or reduce the effects of motion sickness and provide directional indication by potentially communicating with a controlling device such as a personal computer, an application on a mobile device, or some other controlling device, to provide physical sensation in accordance with the directions given by the controlling device. For example, a user may play a virtual reality game in which a user character or avatar is being affected by a strong force of wind. If this device were placed on a user's head and face as shown, the device may produce a tactile sensation to give him or her the sensation of air or wind brushing up against the part of his or her head that faces the direction of the wind, to cause a user to feel a sensation matching the display of the breeze. In this way, the virtual reality experience provided may be enhanced, to help reduce the effects of motion sickness, and provide tactile sensations for directional movement and orientation as well as certain interactions in such a video game, according to some embodiments. Other similar designs for directional movement being translated into tactile sensations may be utilized, as needed, and configuration settings in a controller or application may be able to account for such devices being mounted in differing configurations or orientations.

This full-head embodiment may be particularly useful in neural rehabilitation by stimulating particular regions of the brain. For individuals with brain impairments (e.g., stroke patients suffering from varying degrees of brain damage), the conventional treatment approach consists of mainly "isolated" neural rehabilitation routines, such as specific bodily movements, speech therapy, and stationary video gameplays. This embodiment of the device improves on existing neural rehabilitation routines by providing synchronized haptic and/or electrical simulation to specific regions of the brain for the targeted user movement or cognitive function. Using sensors and transducers 1030 that convert electrical signals to a tactile sensation such as pressure, vibration, electrical stimulation (including all types of waveform signal), temperature, or airflow, such synchronized haptic and/or electrical simulations for the targeted rehabilitation routines (such as bodily movement or cognitive functions) will improve the overall effectiveness of such rehabilitation routines. Such haptic and/or electrical simulations may be synchronized with the desired rehabilitation routines using transducers 1030 that convert electrical signals to a tactile sensation such as pressure, vibration, electrical stimulation (including all types of waveform signal), temperature, or airflow. The transducers 1030 are located all around the head, covering the entire surface area of the brain. These transducers 1030 may be synchronized with additional sensors or sensory controls (as in a 2D video game or Virtual Reality environment) located at specific locations on the body of a user for the targeted rehabilitation functions to improve the recovery of existing neural networks or the development of new, alternative neural networks around damaged neurons. For example, when a stroke patient with a severe left hemisphere brain damage practices right hand and eye movements (for a given rehabilitation routine), the device will simulate both the posterior parietal cortex region (which is involved in transforming visual information into motor commands) and the central (hand) region of the primary motor cortex.

Figure 11:
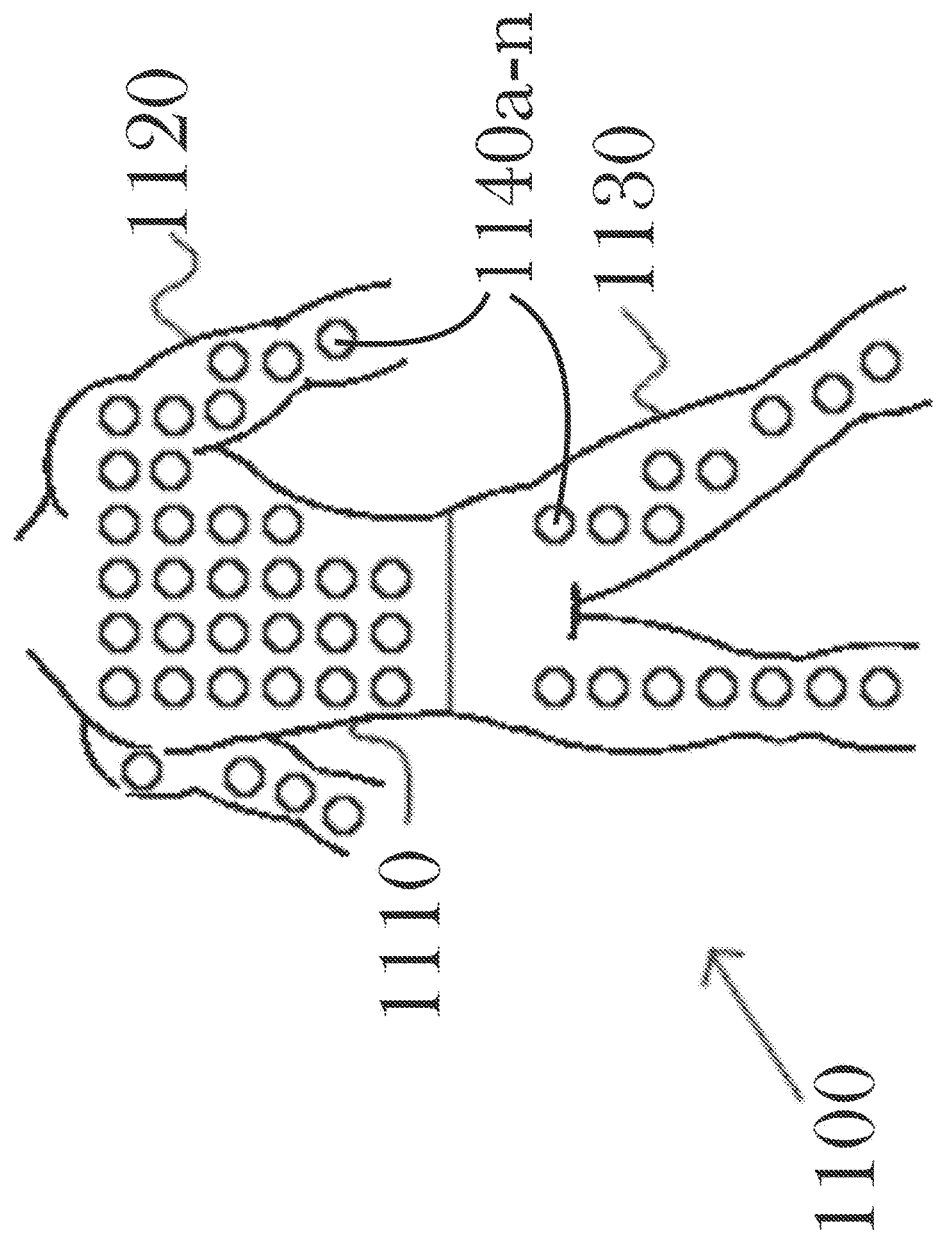
FIG. 11 is a diagram illustrating an exemplary embodiment of a device for motion sickness reduction, directional indication, and neural rehabilitation that may encompass the body as a body-suit.

FIG. 11 is a diagram illustrating an exemplary embodiment of a device for motion sickness reduction and directional indication that may encompass the body as a body-suit 1100. There are three main components to a full-body suit 1100, including a torso portion of the suit 1110, a single or plurality of arm bands, sleeves, or other coverings for the arms 1120, and a single or plurality of leg bands, pantlegs, or other coverings for the legs 1130, each component having a plurality of transducers 1140*a-n*. The construction of each component of a full-body suit may be different from each other, or may be somewhat uniform with materials or techniques, and the construction of any of the components may be metallic, organic, synthetic, of any kind deemed useful for production and use. The use of these components 1110, 1120, 1130 in a full body suit 1100 is to provide for the possibility of full-body haptic feedback according to a virtual reality simulation, to reduce or eliminate motion sickness and aid with directional indications to a user, by attempting to seem more realistic to the user. This system may further be used to reduce motion sickness in a moving vehicle or similar, rather than in only a video game, regardless of whether or not a virtual reality simulation is being executed. The device does not require connection specifically to a virtual reality simulation to operate, but merely connection to a controlling device such as a phone with a controller application, a personal computer, or some other controlling device.

Such a device may be useful for the purposes of direction-based movement aiding to help remediate or reduce the effects of motion sickness and provide directional indication by potentially communicating with a controlling device such as a personal computer, an application on a mobile device, or some other controlling device, to provide physical sensation in accordance with the directions given by the controlling device. For example, a user may play a virtual reality game in which a user character or avatar is being affected by a strong force of wind. If this device were placed on a user's head and face as shown, the device may produce a tactile sensation to give him or her the sensation of air or wind brushing up against the part of his or her head that faces the direction of the wind, to cause a user to feel a sensation matching the display of the breeze. In this way, the virtual reality experience provided may be enhanced, to help reduce the effects of motion sickness, and provide tactile sensations for directional movement and orientation as well as certain interactions in such a video game, according to some embodiments. Other similar designs for directional movement being translated into tactile sensations may be utilized, as needed, and configuration settings in a controller or application may be able to account for such devices being mounted in differing configurations or orientations.

Figure 12:
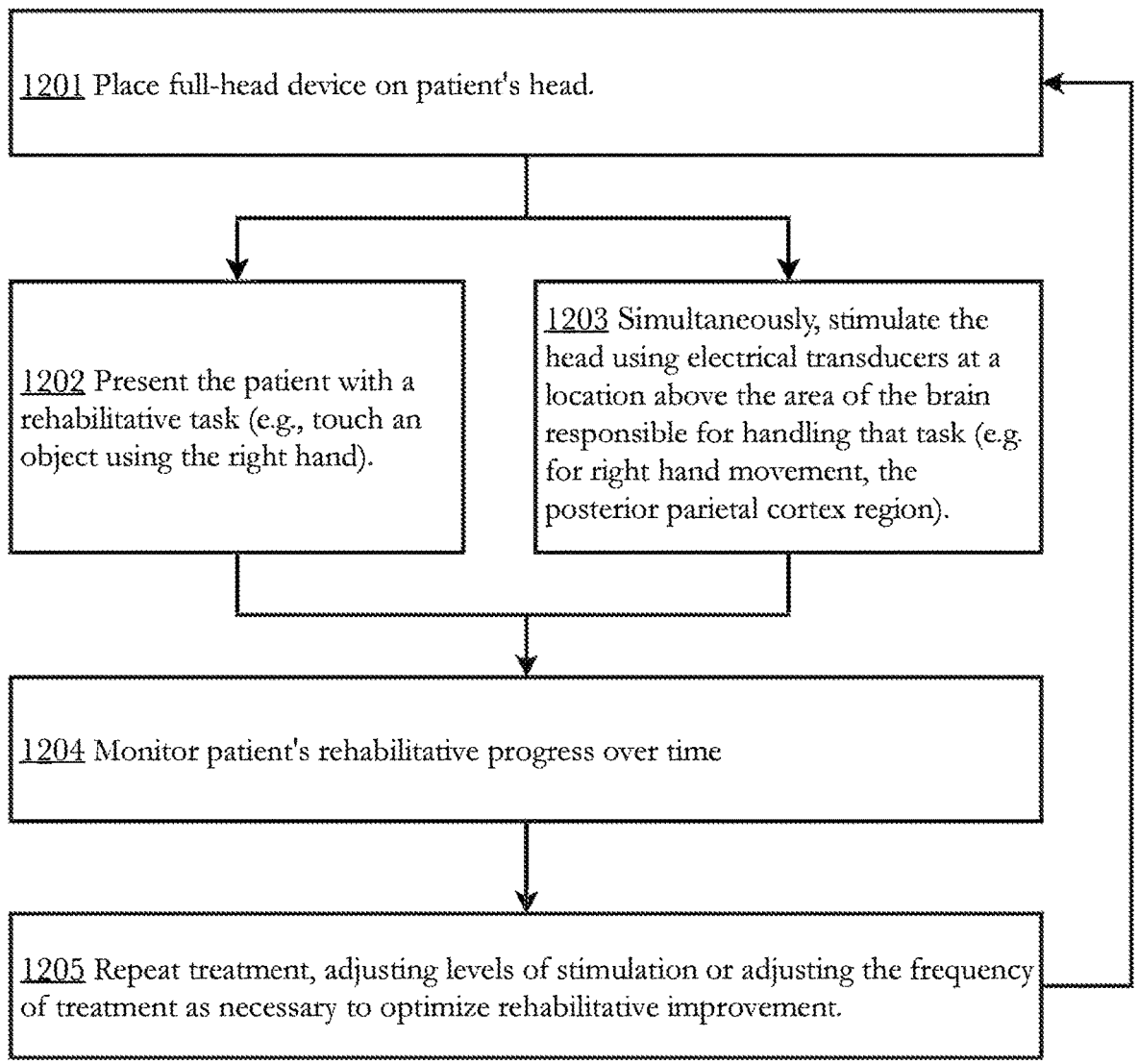
FIG. 12 is a method diagram showing an exemplary process for enhanced neural rehabilitation.

FIG. 12 is a method diagram showing an exemplary process for enhanced neural rehabilitation. Initially, the full-head embodiment of the device is placed on a patient's head 1201. The patient is then presented with a rehabilitative task, usually a physical task such as moving a part of the body (e.g., asking the patient to touch an object with his or her right hand) 1202. While the patient is performing the task, simultaneously stimulate the head using electrical transducers at a location above the area of the brain responsible for handling that task (e.g. for right hand movement, the posterior parietal cortex region) 1203. Optionally, monitor the patient's rehabilitative progress over time 1204, and repeat steps 1201-1203, adjusting levels of stimulation or adjusting the frequency of treatment as necessary to optimize rehabilitative improvement 1205.

Figure 13:
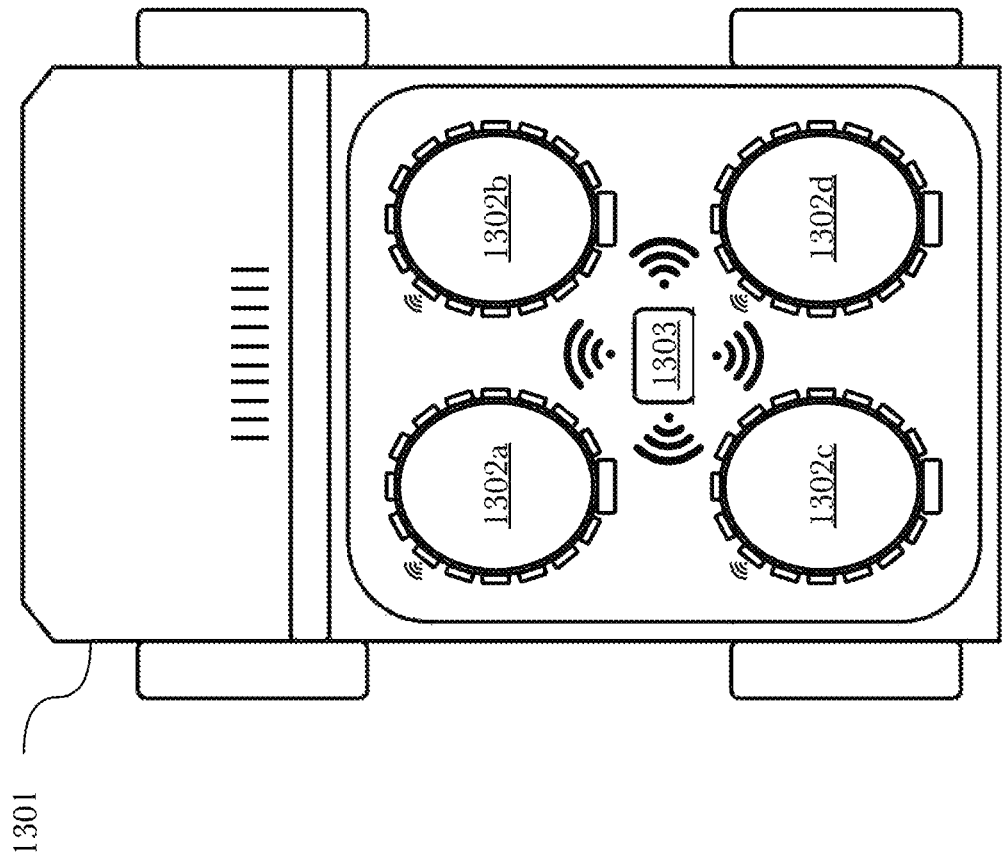
FIG. 13 is a diagram showing an exemplary use of the device by multiple persons sharing a common real-world experience.

FIG. 13 is a diagram showing an exemplary use of the device by multiple persons sharing a common real-world experience. In this exemplary use, four people 1302a-d, each wearing a device, are riding together in a vehicle 1301. The devices worn by each person 1302a-d are each connected wirelessly to a central controller 1303 mounted in the vehicle 1301. The central controller 1303 receives or detects vehicle speed, acceleration, direction, etc., makes appropriate calculations (e.g., for reduction of motion sickness), and sends signals wirelessly to the devices worn by each of the people 1302a-d.

Figure 14:
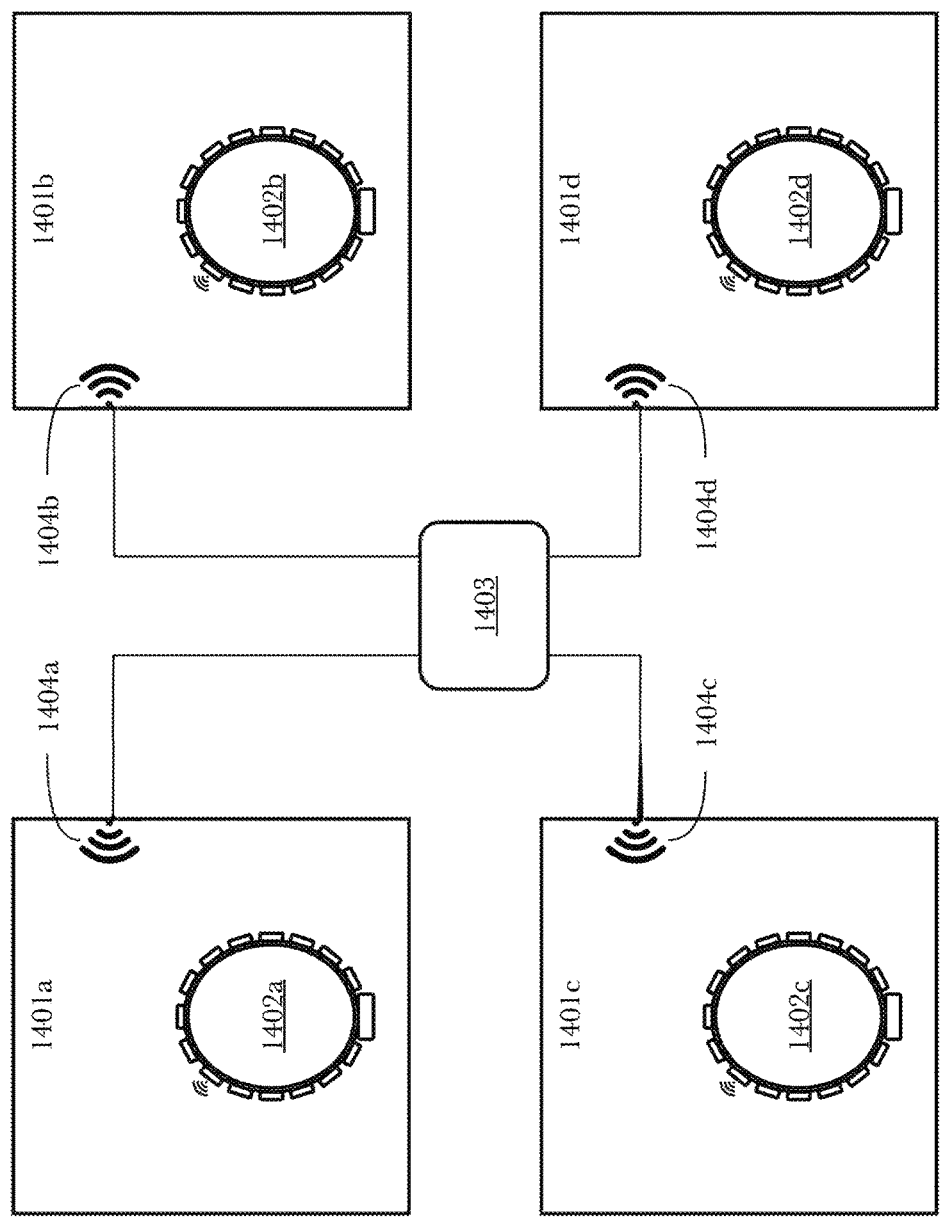
FIG. 14 is a diagram showing an exemplary use of the device by multiple persons sharing a common virtual reality experience.

FIG. 14 is a diagram showing an exemplary use of the device by multiple persons sharing a common virtual reality experience. In this exemplary use, four people 1402a-d, each wearing a device, are located in different locations 1401a-d (e.g., each of the people 1402a-d is sitting at home playing a virtual reality game). The devices worn by each person 1302a-d are each connected wirelessly to wireless routers 1404a-d, which in turn are connected via the Internet to a cloud-based central controller 1403. The central controller 1403 receives information from the virtual reality game regarding in-game speed, acceleration, direction, etc., makes appropriate calculations (e.g., for enhancement of directional sensation), and sends signals to the devices worn by each of the people 1302a-d.

Figure 15:
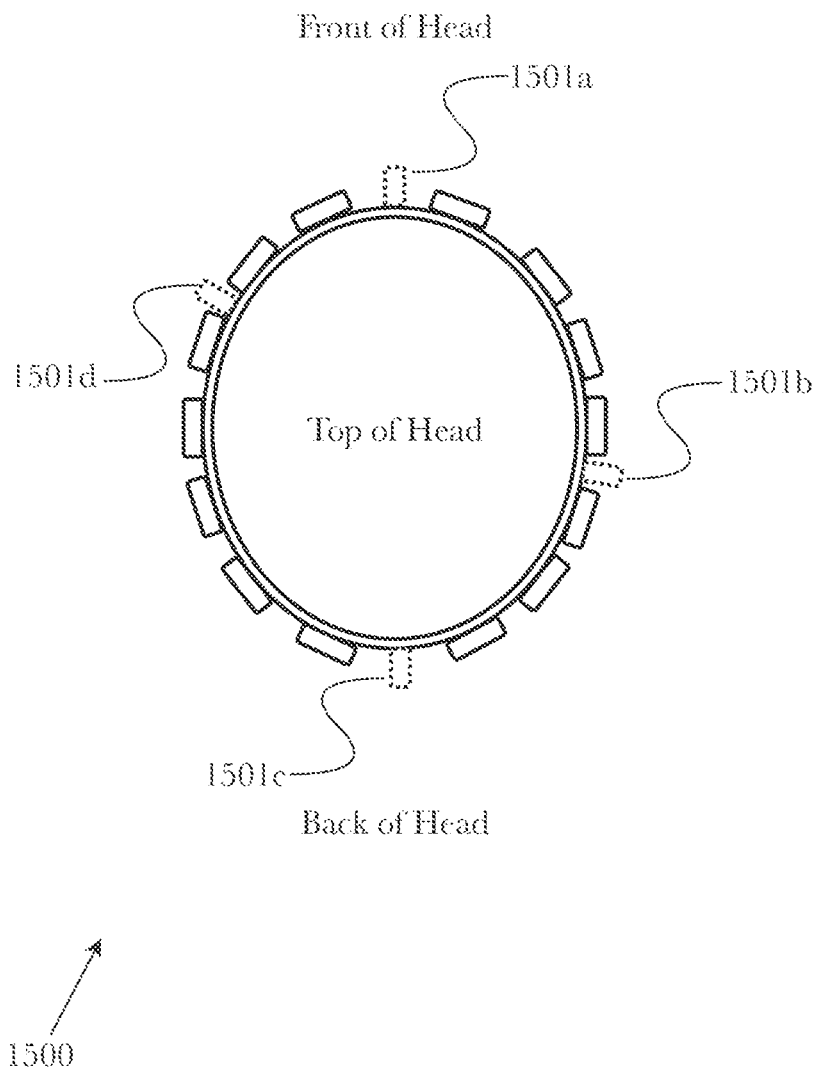
FIG. 15 is a diagram illustrating the modular aspect of the sensor on the headband.

FIG. 15 is a diagram illustrating the modular aspect of the sensor on the headband. A wired or wireless controller may be constructed with a compact profile configured to fit between the transducers on the headband. The controller may have one or a multiple of attachments points 1501a-d on the headband, one between each transducer according to one embodiment. The controller may be attached to the headband via a clip that slides over the headband. The controller may be attached to the headband via a snap button, magnet, hook and loop fastener, etc., where one side of the snap button, magnet, hook and loop fastener is one the controller and the other side being on the headband. The controller may be attached to the headband via another attachment material or method not listed here. The controller may also be permanently attached to the headband between any of the transducers. The headband may have a length of communication wire for moving a wired controller to different positions, the wire being secured or constructed in such a way as to not impede the function of the device.

Figure 20:
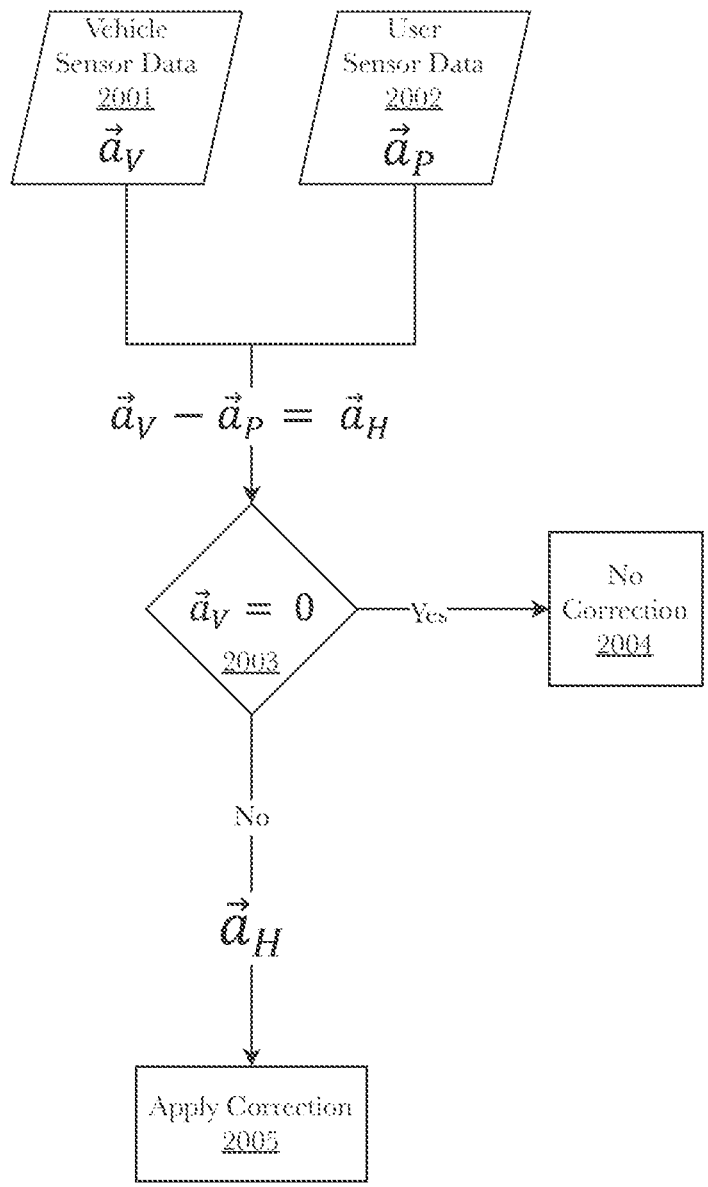
FIG. 20 is a flow diagram showing an exemplary process for correcting for nonvisual but perceivable motion for a motion sickness reduction device.

FIG. 20 is a flow diagram showing an exemplary process for correcting for nonvisual but perceivable motion for a motion sickness reduction device. The method shown here, regarding the systems above, may be implemented on the control unit 1900. The method comprises a first 2001 and second step 2002 of measuring the motion of a vehicle $\vec{a}_V$ and the motion of one or more persons $\vec{a}_P$. The difference is taken in a third step 2003, $\vec{a}_V - \vec{a}_P = \vec{a}_H$, where $\vec{a}_H$ is the acceleration intended for emulation by the headband transducers, and if $\vec{a}_V = 0$, then there is no motion of the vehicle, and thus no correction is needed 2004. If vehicle motion is present, $\vec{a}_V \neq 0$, then the difference, $\Delta \vec{a}$, is sent to the headband for correction 2005.

Figure 21:
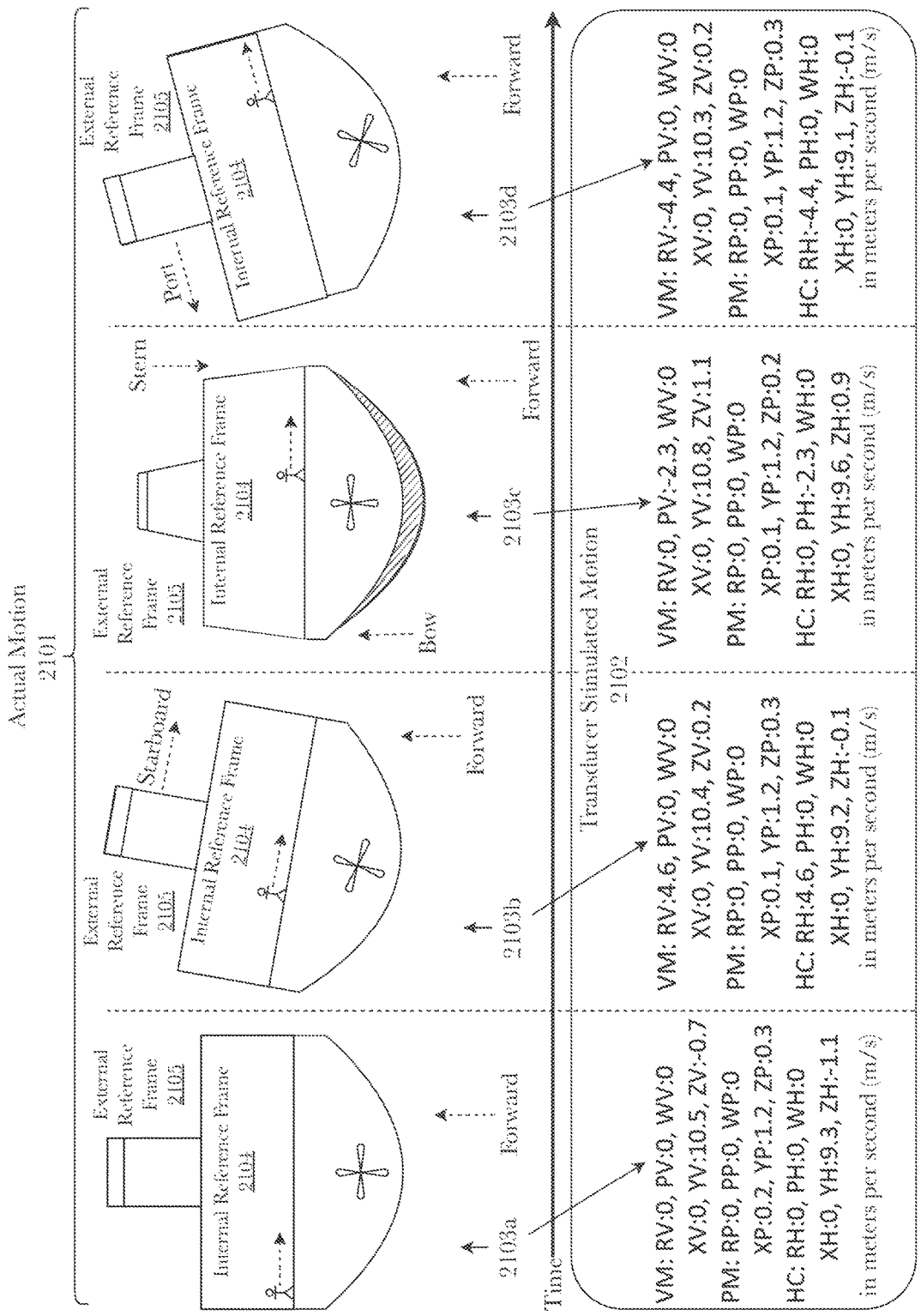
FIG. 21 is a diagram illustrating an example of the exemplary process for correcting for nonvisual but perceivable motion for a motion sickness reduction device.

FIG. 21 is a diagram illustrating an example of the exemplary process for correcting for nonvisual but perceivable motion for a motion sickness reduction device. Using the systems and methods above, motion sickness while riding or on-board a vehicle, such as a ship in motion 2101, may be reduced. For example, 2103a shows a ship that experiences no rocking motion (i.e., roll) as a person begins to walk across the ship, thus using the method above, $\vec{a}_V = 0$, at least in this direction and requires no corrective transducer action 2103b for this vector. As the ship begins to rock to the starboard side 2103b, the person walking will have the difference between their walking velocity/acceleration and the rocking motion of the ship stimulated in his or her headband. The same follows for the frame 2103c where the ship is pitching stern down and for frame 2103d where the is rolling towards the port side.

This example illustrates dual-reference-frame correction of stimulus for a person walking inside a hallway of a large ship. The person's perception of his or her motion within the hallway (an internal reference frame 2104) will not cause motion sickness because the person's visual perception of his or her movement within the hallway matches the persons vestibular perception of his or her movement within the hallway. Therefore, no additional stimulus associated with movement within the hallway is needed to prevent motion sickness. However, as the ship itself is moving in terms of acceleration, deceleration, roll, pitch, and yaw (an external reference frame 2105), the user within the hallway cannot perceive the ship's motion visually, but the user's vestibular system will perceive the ship's motion. Assume for a moment that the user starts walking toward the bow in the hallway while the ship is accelerating forward. If the user starts walking forward walking acceleration is not deducted from the ship's forward acceleration, the amount of stimulus needed to correct for motion sickness will be over-estimated as the combination of the user's forward acceleration and the ship's forward acceleration, when the stimulus only needs to be applied to correct for the ship's forward acceleration (which cannot be perceived visually by the user).

In each frame, the diagram illustrates a set of exemplary values for the motion difference computation. A vehicle's motion is denoted as "VM" and comprises: $\vec{a}_{Roll\ of\ vehicle}$, denoted as "RV", $\vec{a}_{Pitch\ of\ vehicle}$, denoted as "PV", $\vec{a}_{Yaw\ of\ vehicle}$, denoted as WV, $\vec{a}_{X\text{-}axis\ of\ vehicle}$, denoted as "XV", $\vec{a}_{Y\text{-}axis\ of\ vehicle}$, denoted as "YV", and $\vec{a}_{Z\text{-}axis\ of\ vehicle}$, denoted as "ZV". The same follows for a person's motion measurements (PM) where "V" in the variables is replaced with "P". The difference between the "VM" and "PM", i.e., the headband correction (HC), is set as variables with an "H", e.g., "RH", "PH", "WH", and so forth.

As a specific example, consider frame 2103c. The ship experiences no roll or yaw at this point but does experience a dive on the stern side, hence a negative pitch (PV) value. Imagine the ship comprises a plurality of sensors, the sensors nearest the person walking being used to calculate transducer stimulation. Thus, if the person is walking near the bow during a nosedive, there will be an increase in both z-axis (ZV and ZP) heights of the ship and the person. The person's z-axis height may be lower because they were in mid-stride and the force of the ship's bow rising causes them to bend his or her knees. Again, these values are merely exemplary. The corrective values (HC) are then the difference between the person's motion and the ship's motion. The HC values when activated on the headband's transducers give the wearer a sense of the ship's motion from the ship's reference frame and thus allows the wearer's brain to resolve the conflict in motion between what the person sees and what the person feels in his or her vestibular system.

Figure 22:
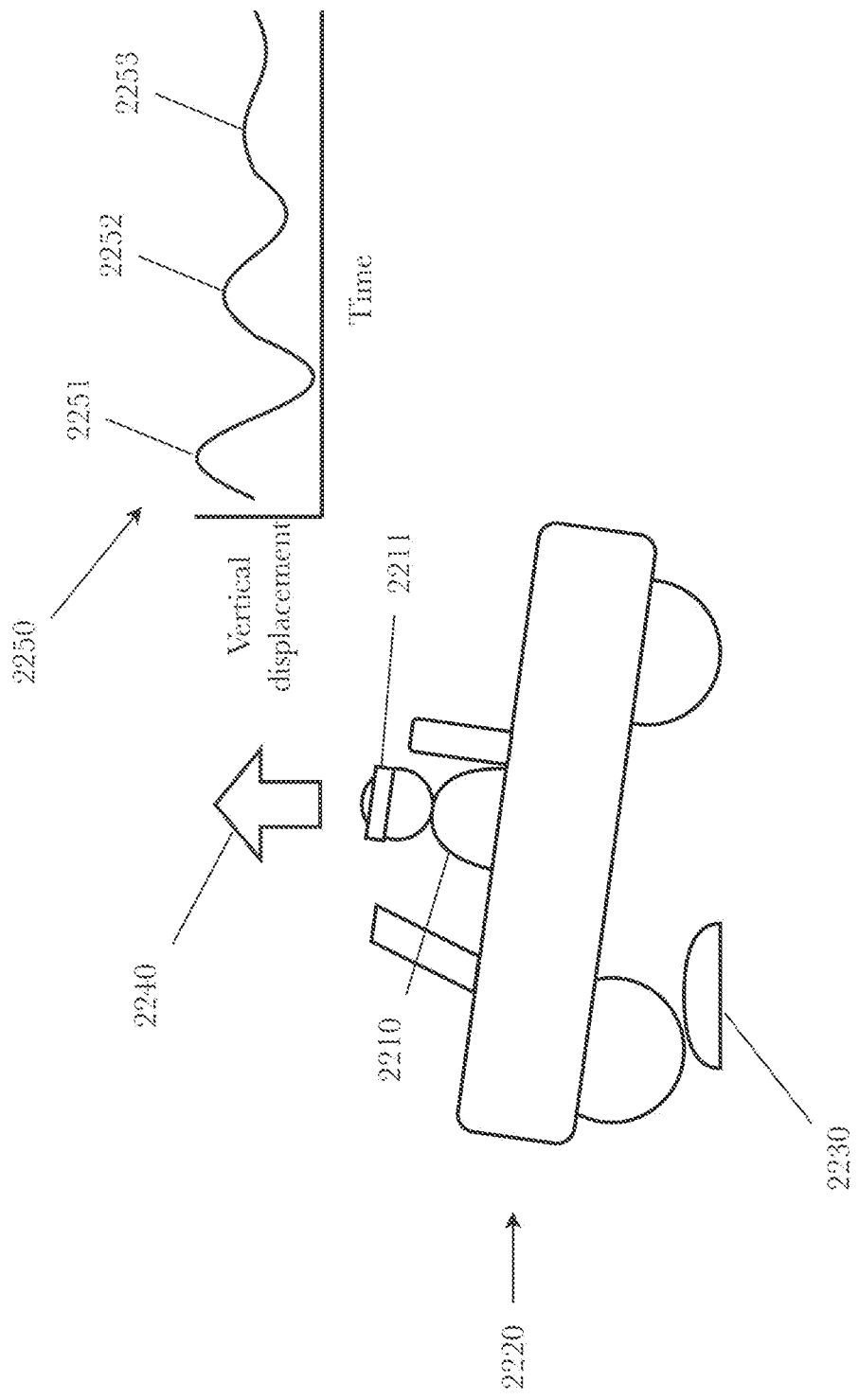
FIG. 22 is a diagram illustrating motion sickness adjustment using decaying vertical displacement feedback.

FIG. 22 is a diagram illustrating motion sickness adjustment using decaying vertical displacement feedback. In this example, a person 2210 wearing a haptic feedback headband 2211 is shown riding in a car 2220 driving over an obstacle 2230 in the road. Driving over the obstacle 2230 causes an upward vertical displacement 2240 of the car 2220, person 2210, and headband 2211. A sensor on the vertical headband detects the vertical displacement, the initial value of which is shown as ref. 2251 of the inset vertical displacement graph 2250. In vehicles such as cars, our brains have developed an expectation of decaying oscillation after a vertical displacement such as that shown in the vertical displacement graph 2250 with decaying amplitude shown by the decreasing peaks in the graph 2251, 2252, 2253. A decaying vertical oscillation can be simulated to reduce motion sickness. For example, as discussed above, vertical motion may be represented by operation of some or all of the transducers simultaneously. Other configurations of transducers could be used such as a transducer on the top of the head, or transducers arranged vertically along the longitudinal axis of the body. The decaying vertical oscillation of the vehicle can either be represented by the transducers directly by measurement of the actual decaying oscillation, enhanced by adding to or deducting from the amplitude and/or frequency of actual decaying oscillation, or by simulating a decaying oscillation via application of a decaying sine wave, decaying square wave, decaying triangle wave, or similar decaying wave functions.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 23:
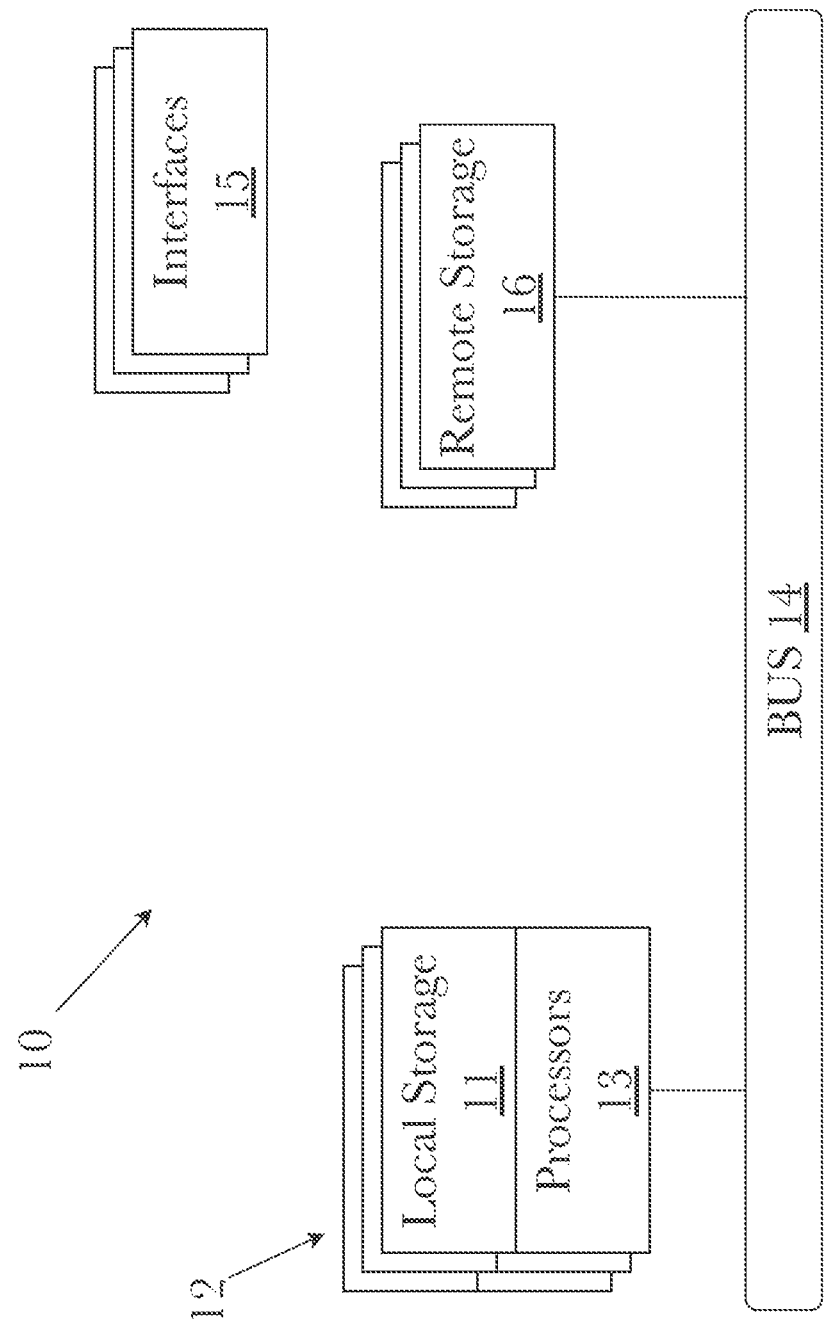
FIG. 23 is a block diagram illustrating an exemplary hardware architecture of a computing device.

Referring now to FIG. 23, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network, a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 23 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 24:
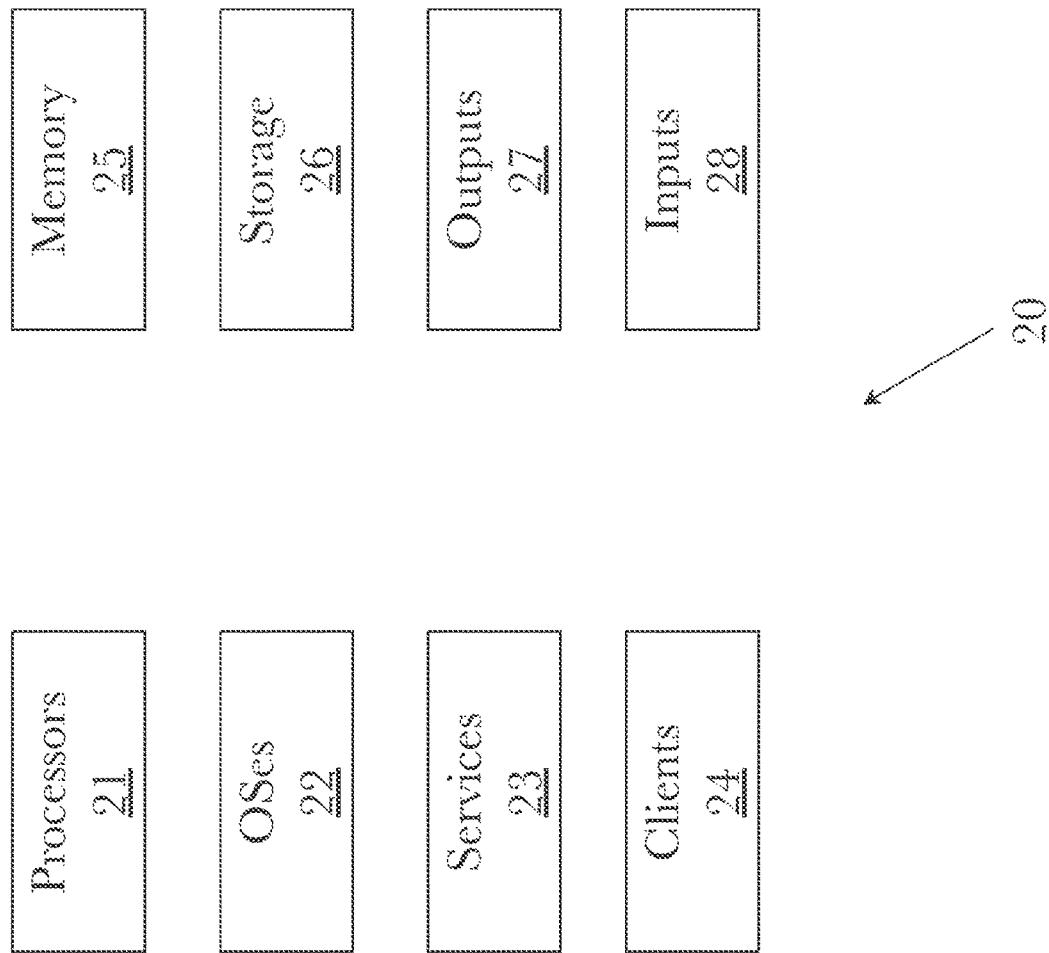
FIG. 24 is a block diagram illustrating an exemplary logical architecture for a client device.

In some aspects, systems may be implemented on a standalone computing system. Referring now to FIG. 24, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 23). Examples of storage devices 26 include flash memory, magnetic hard drive, CD-ROM, and/or the like.

Figure 25:
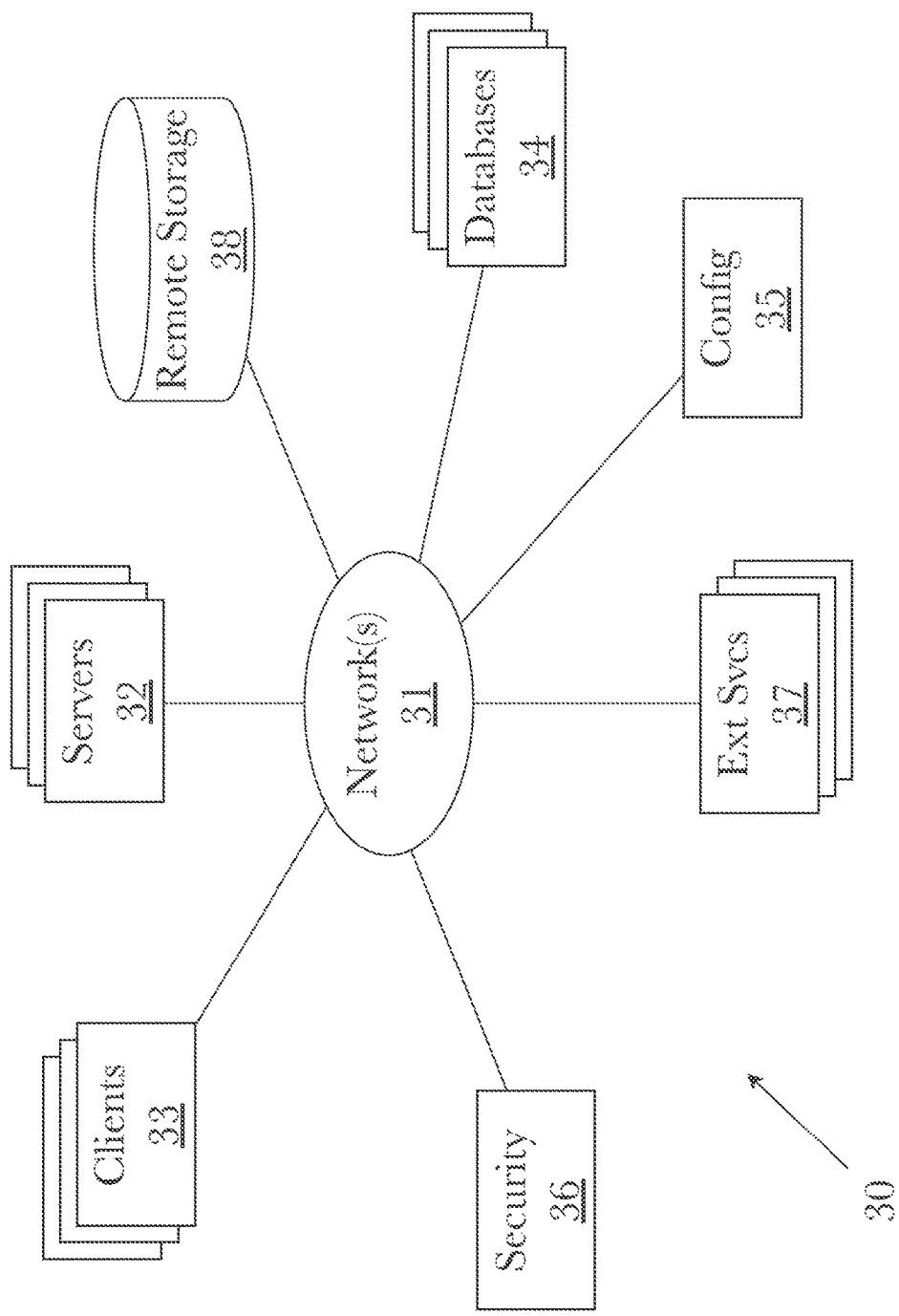
FIG. 25 is a block diagram showing an exemplary architectural arrangement of clients, servers, and external services.

In some aspects, systems may be implemented on a distributed computing network, such as one having any number of clients and/or servers. Referring now to FIG. 25, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 24. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 26:
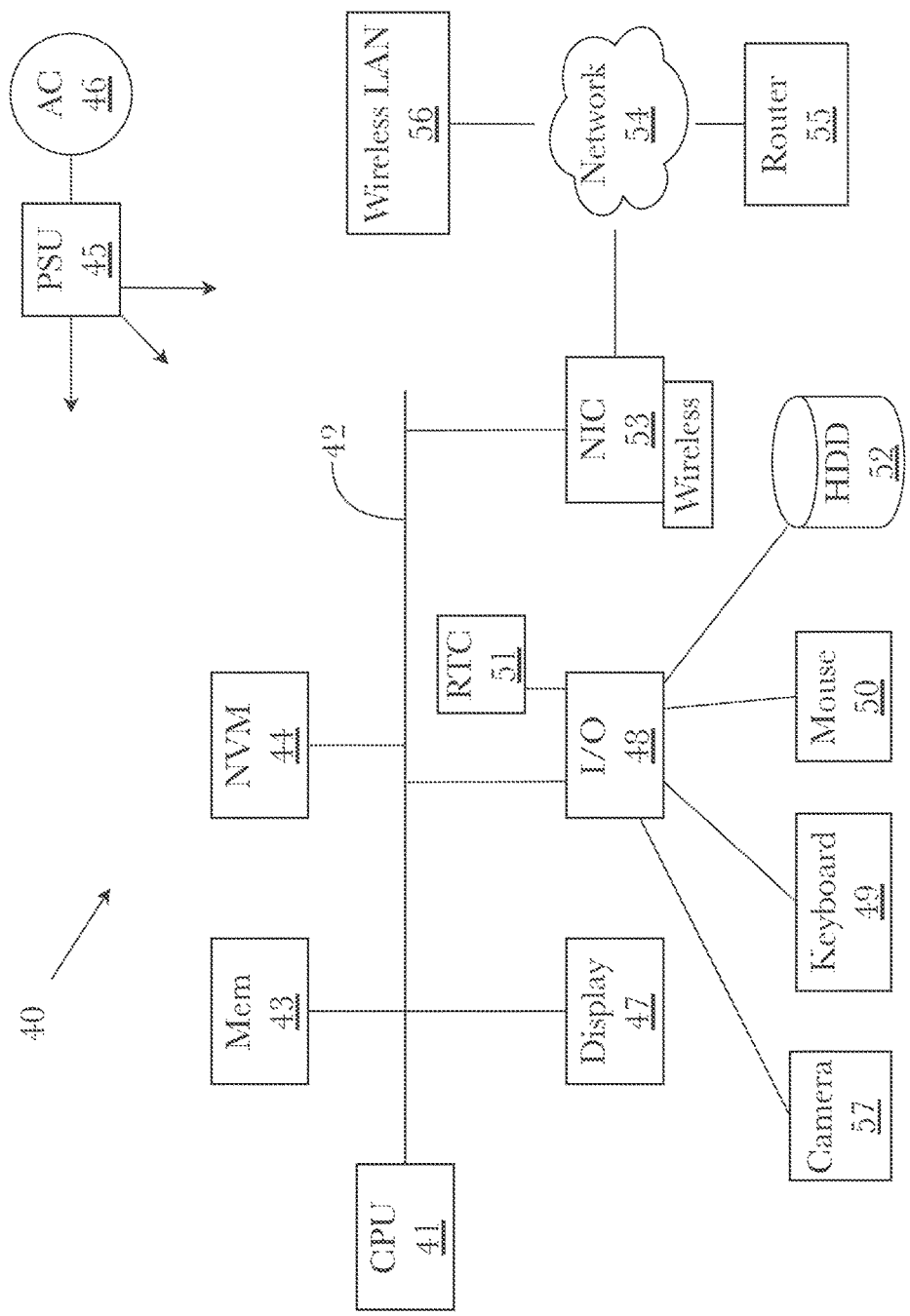
FIG. 26 is another block diagram illustrating an exemplary hardware architecture of a computing device.

FIG. 26 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A device for motion sickness reduction associated with physical movement, comprising:
    an annular-shaped headband configured to be worn about a horizontal circumference of a human head, the headband having a circumference and comprising:
        a plurality of transducers arranged about the circumference of the headband, each transducer being configured to provide haptic feedback to a wearer of the headband; and
        a first sensor configured to periodically measure motion of the headband;
        a controller comprising a processor, a memory, and a plurality of programming instructions stored in the memory which, when operating on the processor, cause the controller to:
            receive motion data from the first sensor, the motion data indicating the direction and the magnitude of the motion of the headband;
            receive data pertaining to motion of an external reference frame from a second sensor;
            determine a differential motion between the headband and the motion of the external reference frame;
            identify a first transducer of the plurality of transducers that is closest in direction to the direction of the differential motion;
            operate the first transducer, the intensity of transducer operation corresponding to the magnitude of the differential motion;
            while the magnitude of the differential motion meets or exceeds a threshold value, operate a plurality of additional transducers on either side of the first transducer, the intensity of operation of the plurality of additional transducers corresponding to the magnitude of the differential motion, but at a lower intensity than the operation of the first transducer;
            while the magnitude of the difference in differential motion is below the threshold value, cease the operation of the plurality of additional transducers; and
            repeating the operations of the controller set forth above as the differential motion data is recomputed as new data is received from the sensors.

2. The device of claim 1, wherein the motion data comprises one or a combination of the headband's position, speed, velocity, or acceleration.

3. The device of claim 2, wherein, when a new direction of the differential motion is detected from sensor data and a newly-selected first transducer is selected by the controller to reflect the new direction, one or more transducers are activated in sequence between the previously-selected first transducer and the newly-selected first transducer to indicate a rotational transition from the old direction to the new direction.

4. The device of claim 3, wherein the intensity of operation of the one or more transducers activated in sequence is gradually reduced in the reverse order of their activation so as to cause a trailing off of intensity following the indication of rotational transition.

5. The device of claim 1, wherein the haptic feedback is in the form of pressure, vibration, or electrical stimulation.

6. The device of claim 4, wherein the haptic feedback is in the form of pressure, vibration, or electrical stimulation.

7. A method for motion sickness reduction associated with physical movement, comprising the steps of:
    periodically receiving, at a controller, motion data from a first and a second sensor, the motion data from the first sensor indicating a direction and a magnitude of motion of a headband comprising a plurality of transducers and the motion data from the second sensor indicating a direction and a magnitude of motion of an external reference frame;
    determining a differential motion between the external reference frame and the headband;
    identifying a first transducer of the plurality of transducers that is closest in direction to the direction of the differential motion;
    operating the first transducer, the intensity of transducer operation corresponding to the magnitude of the differential motion;
    while the magnitude of the differential motion meets or exceeds a threshold value, operating a plurality of additional transducers to either side of the first transducer, the intensity of operation of the plurality of additional transducers corresponding to the magnitude of the differential motion, but at a lower intensity than the operation of the first transducer;
    while the magnitude of the differential motion falls below the threshold value, ceasing the operation of the plurality of additional transducers; and
    repeating the operations of the controller set forth above as the differential motion data is recomputed as new data is received from the sensors.

8. The method of claim 7, wherein the motion data comprises one or a combination of the headband's position, speed, velocity, or acceleration.

9. The method of claim 8, wherein, when a new direction of the differential motion is detected from sensor data and a newly-selected first transducer is selected by the controller to reflect the new direction, one or more transducers are activated in sequence between the previously-selected first transducer and the newly-selected first transducer to indicate a rotational transition from the old direction to the new direction.

10. The method of claim 9, wherein the intensity of operation of the one or more transducers activated in sequence is gradually reduced in the reverse order of their activation so as to cause a trailing off of intensity following the indication of rotational transition.

11. The method of claim 7, wherein the haptic feedback is in the form of pressure, vibration, or electrical stimulation.

12. The method of claim 10, wherein the haptic feedback is in the form of pressure, vibration, or electrical stimulation.

13. A device for motion sickness reduction associated with physical movement, comprising:
- an annular-shaped headband configured to be worn about a horizontal circumference of a human head and comprising:
  - a plurality of transducers arranged about a circumference of the headband, each transducer being configured to provide haptic feedback to a wearer of the headband; and
  - a sensor configured to periodically measure motion of the headband;
- a controller comprising a processor, a memory, and a plurality of programming instructions stored in the memory which, when operating on the processor, cause the controller to:
  - receive motion data from the sensor, the motion data indicating a direction and a magnitude of the motion of the headband;
  - identify a first transducer of the plurality of transducers that is closest in direction to the direction of the motion;
  - operate the first transducer, the intensity of transducer operation corresponding to the magnitude of the motion;
  - while the magnitude of the motion meets or exceeds a threshold value, operate a plurality of additional transducers to either side of the first transducer, the intensity of operation of the plurality of additional transducers corresponding to the magnitude of the motion, but at a lower intensity than the operation of the first transducer;
  - while the magnitude of the motion falls below the threshold value, cease the operation of the plurality of additional transducers; and
  - repeat the operations of the controller set forth above as new motion data is received from the sensor.

14. The device of claim 13, wherein the motion data comprises one or a combination of the headband's position, speed, velocity, or acceleration.

15. The device of claim 14, wherein, when a new direction of the motion is determined and a newly-selected first transducer is selected by the controller to reflect the new direction, one or more transducers are activated in sequence between the previously-selected first transducer and the newly-selected first transducer to indicate a rotational transition from the old direction to the new direction.

16. The device of claim 15, wherein the intensity of operation of the one or more transducers activated in sequence is gradually reduced in the reverse order of their activation so as to cause a trailing off of intensity following the indication of rotational transition.

17. The device of claim 13, wherein the haptic feedback is in the form of pressure, vibration, or electrical stimulation.

18. The device of claim 16, wherein the haptic feedback is in the form of pressure, vibration, or electrical stimulation.

* * * * *